(12) United States Patent
Lee et al.

(10) Patent No.: US 11,684,284 B2
(45) Date of Patent: Jun. 27, 2023

(54) CARBON FIBER OPTRODES FOR MAGNETIC RESONANCE IMAGING COMPATIBLE OPTOGENETICS

(71) Applicant: The Board of Trustees of the Leland Stanford Junior University, Stanford, CA (US)

(72) Inventors: Jin Hyung Lee, Stanford, CA (US); Ben A. Duffy, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 531 days.

(21) Appl. No.: 15/743,174

(22) PCT Filed: Jul. 20, 2016

(86) PCT No.: PCT/US2016/043179
§ 371 (c)(1),
(2) Date: Jan. 9, 2018

(87) PCT Pub. No.: WO2017/015395
PCT Pub. Date: Jan. 26, 2017

(65) Prior Publication Data
US 2018/0199850 A1    Jul. 19, 2018

Related U.S. Application Data

(60) Provisional application No. 62/195,260, filed on Jul. 21, 2015.

(51) Int. Cl.
*A61B 5/055*     (2006.01)
*A61B 5/00*      (2006.01)
(Continued)

(52) U.S. Cl.
CPC ............ *A61B 5/055* (2013.01); *A61B 5/0084* (2013.01); *A61B 5/4041* (2013.01); *A61N 1/05* (2013.01);
(Continued)

(58) Field of Classification Search
CPC ..... A61B 5/0084; A61B 5/055; A61B 5/4041; A61N 1/05; A61N 1/086; A61N 2005/063;
(Continued)

(56) References Cited

U.S. PATENT DOCUMENTS

| 5,683,444 A | 11/1997 | Huntley et al. |
| 6,475,661 B1 * | 11/2002 | Pellegri ................. H01M 8/188 |
| | | 429/105 |

(Continued)

FOREIGN PATENT DOCUMENTS

| WO | WO 2010056970 | 5/2010 |
| WO | WO 2010103174 | 9/2010 |

(Continued)

OTHER PUBLICATIONS

Armstrong et al., (2013) "Closed-Loop Optogenetic Intervention in Mice", Nat Protoc. 8(8): 1475-1493.
(Continued)

*Primary Examiner* — Michael T Rozanski
(74) *Attorney, Agent, or Firm* — Rudy J. Ng; Paula A. Borden; Bozicevic, Field & Francis LLP

(57) ABSTRACT

The present disclosure provides a device for carrying out magnetic resonance imaging compatible optogenetics; and methods for using the device.

20 Claims, 9 Drawing Sheets

(51) Int. Cl.
*A61N 1/05* (2006.01)
*A61N 5/06* (2006.01)
*A61N 1/08* (2006.01)
*A61N 5/067* (2006.01)

(52) U.S. Cl.
CPC .......... *A61N 1/086* (2017.08); *A61N 5/0622* (2013.01); *A61N 5/067* (2021.08); *A61N 2005/063* (2013.01); *A61N 2005/0651* (2013.01)

(58) Field of Classification Search
CPC ...... A61N 2005/0651; A61N 2005/067; A61N 5/0622
See application file for complete search history.

(56) References Cited

U.S. PATENT DOCUMENTS

| | | | | |
|---|---|---|---|---|
| 6,605,390 | B1* | 8/2003 | Moore | H01M 4/136 429/231.8 |
| 8,936,630 | B2 | 1/2015 | Denison et al. | |
| 2005/0245708 | A1* | 11/2005 | Tada | C08F 8/00 526/250 |
| 2007/0060984 | A1 | 3/2007 | Webb et al. | |
| 2009/0093403 | A1 | 4/2009 | Zhang et al. | |
| 2009/0252459 | A1* | 10/2009 | Nielson | G02B 6/3885 385/79 |
| 2010/0145418 | A1 | 6/2010 | Zhang et al. | |
| 2011/0306847 | A1 | 12/2011 | Lowry et al. | |
| 2012/0253261 | A1 | 10/2012 | Poletto et al. | |
| 2013/0046148 | A1 | 2/2013 | Tathireddy et al. | |
| 2013/0237906 | A1 | 9/2013 | Park et al. | |
| 2014/0350375 | A1* | 11/2014 | Wolfe | H01L 33/382 600/377 |
| 2015/0040249 | A1* | 2/2015 | Deisseroth | A61B 5/4076 800/9 |

FOREIGN PATENT DOCUMENTS

| | | |
|---|---|---|
| WO | WO 2011116238 | 9/2011 |
| WO | WO 2015148974 | 10/2015 |

OTHER PUBLICATIONS

Dunn et al., (2009) "Functional Brain Mapping at 9.4t Using a New Mri Compatible Electrode Chronically Implanted in Rats", Magn Reson Med. 61(1): 222-228.

Shyu et al., (2004) "Bold Response to Direct Thalamic Stimulation Reveals a Functional Connection Between the Medial Thalamus and the Anterior Cingulate Cortex in the Rat", Magnetic Resonance in Medicine 52:47-55.

Wang et al., (2012) "Integrated Device for Combined Optical Neuromodulation and Electrical Recording for Chronic in vivo Applications", Journal of Neural Engineering 9(016001) 14 pages.

* cited by examiner

CARBON FIBER OPTRODES FOR MAGNETIC RESONANCE IMAGING COMPATIBLE OPTOGENETICS

CROSS-REFERENCE TO RELATED APPLICATIONS

This application is a U.S. National Stage Entry of International Application No. PCT/US2016/043179, filed Jul. 20, 2016, which claims priority pursuant to 35 U.S.C. § 119(e) to the filing date of U.S. Provisional Application No. 62/195,260, filed Jul. 21, 2015, the disclosures of which are incorporated herein by reference.

GOVERNMENT SUPPORT CLAUSE

This invention was made with Government support under contracts EB008738, OD007265, AG047666, and NS087159 awarded by the National Institutes of Health and under contract 1460400 awarded by the National Science Foundation. The Government has certain rights in the invention.

INTRODUCTION

Optogenetic functional magnetic resonance imaging (ofMRI) is a powerful new technique based on combining optogenetics with functional magnetic resonance imaging (fMRI). Optogenetics allows temporally precise and cell-type specific modulation of neural activity, while fMRI allows us to visualize this at the whole-brain level. ofMRI is likely to play an important role in dissecting functional networks. However, it relies on measuring hemodynamic changes, in particular the blood oxygenation level-dependent (BOLD) signal, which is a surrogate measure of changes in neural activity. Most studies using fMRI in animal models do not employ other measures of neural activity, e.g. electroencephalography (EEG), local field potentials (LFPs), multi-unit recordings or single-unit recordings. This is primarily because implanted electrodes and connectors can cause severe degradation of magnetic resonance images due to differences in magnetic susceptibility, which in turn leads to static field inhomogeneity and susceptibility artifacts.

Many studies have attempted to reduce the artifacts associated with electrodes for electrophysiological recordings in small animals. Successful attempts at MRI compatible recordings include the use of carbon fiber (CF) electrodes placed on the skull or surface of the brain (Austin et al., 2003; David et al., 2008; Mirsattari et al., 2005; Nersesyan et al., 2004; Opdam et al., 2002), calomel electrodes anchored to the skull (Brinker et al., 1999), platinum wire electrodes covering the scalp (Sumiyoshi et al., 2011), saline-filled (Canals et al., 2009; Moreno et al., 2015) or carbon fiber-threaded (Moreno et al., 2015; Shyu et al., 2004) glass micropipettes inserted into the brain. Many of these designs are only suited to recording in head-fixed animals and are therefore not suitable for chronic optogenetics studies. There have been far fewer reports on the use of high-field MRI compatible depth electrodes for long-term LFP recording and/or stimulation. Recently, Dunn et al. demonstrated that this is achievable without causing significant artifacts by coating carbon fiber bundles in polyvinylidene fluoride (PVDF) for insulation and rigidity (Dunn et al., 2009). Further studies have shown that susceptibility artifacts caused by chronically implanted ultra-fine (36-50 μm) tungsten electrodes can be tolerable, even in highly T2* weighted images that are particularly sensitive to magnetic field inhomogeneity (Chao et al., 2014; Huttunen et al., 2008; Lai et al., 2014). Alternatively, to minimize susceptibility effects from implanted electrodes, some researchers insert electrodes at a less than 90° angle from the rostral-caudal plane, although this requires a more skillful surgical procedure (Englot et al., 2008). Despite the multitude of studies using implanted electrodes, there has yet to be a systematic comparison between different implantable electrodes for long-term recording or combined stimulation including optogenetics.

SUMMARY

The present disclosure provides a device for carrying out magnetic resonance imaging compatible optogenetics; and methods for using the device.

Aspects of the present disclosure include an implantable device comprising an optrode comprising a carbon fiber electrode, wherein the carbon fiber electrode has a diameter of from 10 μm to 180 μm.

In some embodiments, the carbon fiber electrode has a diameter of from 100 μm to 150 μm.

In some embodiments, the carbon fiber electrode comprises a bundle of carbon fibers.

In some embodiments, the bundle of carbon fibers comprises 1000 or less carbon fibers.

In some embodiments, the carbon fiber electrode comprises an insulation coating.

In some embodiments, the carbon fiber electrode is attached to a metal wire or a metal connector with a conductive adhesive.

In some embodiments, the conductive adhesive is a conductive epoxy adhesive.

In some embodiments, the carbon fiber electrode has an impedance magnitude of 200 kΩ or less at 100 Hz in 0.9% (w/v) sodium chloride in water.

In some embodiments, the optrode is adapted for use in magnetic resonance imaging.

In some embodiments, the device further includes a light source.

In some embodiments, the light source comprises an optical fiber.

In some embodiments, the light source comprises a laser.

Aspects of the present disclosure also include a method for monitoring activity in an excitable organ or tissue. The method includes: a) surgically implanting the device of the present disclosure into an excitable organ or tissue of a subject; and b) monitoring the activity of the organ or tissue by: i) conducting functional magnetic resonance imaging on the organ or tissue, wherein the organ or tissue comprises cells that express one or more light-responsive polypeptides; and/or ii) recording a detectable parameter of the organ or tissue using the device.

In some embodiments, the detectable parameter comprises one or more of local field potentials, single-unit activity, and multi-unit activity in the organ or tissue.

In some embodiments, the monitoring comprises chronically monitoring the activity of the organ or tissue.

In some embodiments, the recording is performed 10 days or more after implanting the device.

In some embodiments, the one or more light-responsive polypeptides comprises a hyperpolarizing light-responsive polypeptide.

In some embodiments, the one or more light-responsive polypeptides comprises a depolarizing light-responsive polypeptide.

In some embodiments, the device comprises a light source, and the method comprises delivering light to the organ or tissue using the light source.

In some embodiments, the light source comprises an optical fiber.

BRIEF DESCRIPTION OF THE DRAWINGS

(FIG. 1, panel a) 105 μm core diameter fiber optic was stripped of its plastic coating, and cleaved to a predetermined length. The end of the fiber (black triangle) appeared to be flat and free of cracks when viewed under a light microscope. (FIG. 1, panel b) The fiber was then inserted into the concave end of a 1.25 mm ceramic ferrule and secured with epoxy adhesive. A correctly inserted fiber optic appeared flush with the convex end of the ferrule. (FIG. 1, panel c) The end of the ferrule was checked under a light microscope to ensure that light passed unobstructed through the fiber optic. (FIG. 1, panel d) 1K carbon fiber tow was separated into two bundles, and each bundle was separated again to make four 0.25K bundles from one 1K bundle. (FIG. 1, panel e) Each 0.25K bundle was then attached to a section of wire using silver conductive epoxy, and coated with three layers of a PVDF solution. Finished carbon fiber electrodes appeared straight and evenly coated. (FIG. 1, panel f) A carbon fiber electrode and implantable fiber optic were secured together using epoxy adhesive. When viewing the optrode under a light microscope (right panel), the electrode and fiber optic ran parallel to each other. (FIG. 1, panel g) Unused contacts were removed from the press fit connector, and to complete the assembly, the implant was soldered opposite a brass screw, which was used as a reference electrode. (FIG. 1, panel h) Completed implants were surgically implanted into Sprague-Dawley rats.

(FIG. 2, panel a) FSE MRI image of different electrodes embedded in an agarose phantom. (FIG. 2, panel b) 1D profiles of the signal intensity through the center of each electrode in the phantom averaged across 7 slices showing signal void (as a percentage of local signal intensity) vs. distance from center of electrode. (FIG. 2, panel c to FIG. 2, panel e) In vivo structural (FSE) and functional 4-interleave spiral readout GRE (average of 520 frames) MRI images showing rats implanted with optrodes constructed out of (FIG. 2, panel c) tungsten microwire, (FIG. 2, panel d) 1K CF and (FIG. 2, panel e) 0.25K CF electrodes. (FIG. 2, panel f) Standard SPGR with rectilinear sampling comparing tungsten and 0.25K CF electrodes. (FIG. 2, panel g) Mean 1D profiles for the spiral readout functional MRI images of the signal intensity through the center of each optrode for each of the different designs. Error bars represent the standard error of the mean. Tungsten (n=5), 1K CF (n=4), 0.25K CF (n=4). (FIG. 2, panel h) Example LFP recordings and average power within different LFP frequency bands for tungsten (n=2) and 0.25K CF electrodes (n=3) measured in awake rats 2-3 months after implantation.

(FIG. 3, panel a) Left panel—schematic indicating location of stimulation (blue triangle) and recording electrode line (black line). Middle panel—50 μm thick coronal section showing EYFP expression in the right hippocampus. Right panel—location of imaging slices 1-20. (FIG. 3, panel b) T-statistic map from block-design (20 s-on, 40 s-off) subthreshold stimulation of the hippocampus (average over 3 trials). (FIG. 3, panel c) fMRI time course (average of 3 trials and single trial) shown for the block-design stimulation paradigm. (FIG. 3, panel d) Single trial simultaneously recorded EEG shown for the Beta band 13-30 Hz. (FIG. 3, panel e) Spectrogram of the EEG recording during fMRI acquisition. Abbreviations: HF—Hippocampal Formation, Sep—Septum.

(FIG. 4, panel a) GLM design matrix for the fMRI analysis. (FIG. 4, panel b) T-statistic map showing regions of significant BOLD signal change during a seizure-inducing stimulation (average of 2 trials). (FIG. 4, panel c) T-statistic map showing regions of significant BOLD signal change during the first 20 s an epileptiform afterdischarge. Site of optical stimulation is marked by the white triangle. (FIG. 4, panel d) Segmentation of 4 different ROIs. (FIG. 4, panel e) fMRI time course shown for a single trial. (FIG. 4, panel f) Single trial simultaneously recorded LFP shown for the Beta band 13-30 Hz. (FIG. 4, panel g) Spectrogram of the LFP recording during fMRI acquisition. (FIG. 4, panel h) fMRI time course for the single trial shown from the ipsilateral hippocampus, septum and contralateral hippocampus. Duration of optical stimulations is marked by blue bars. T-statistic maps were thresholded at a significance level of $p<0.01$, voxel-wise FDR corrected. Abbreviations: Acb—Accumbens Nucleus, Cpu—Caudate Putamen, RS—Retrosplenial Cortex, Thal—Thalamus, Cg—Cingulate Cortex, HF—Hippocampal Formation, S1—Primary Somatosensory Cortex, Sep—Septum.

(FIG. 5, panel a) First-level (fixed-effects) t-statistic map showing voxels which were significantly activated during subthreshold optogenetic stimulation at 20 Hz. (FIG. 5, panel b) First-level (fixed-effects) t-statistic map showing voxels which were significantly activated during seizure-like afterdischarges. Group-level T-statistic maps were thresholded at a significance level of $p<0.001$, voxel-wise FDR corrected. (FIG. 5, panel c) fMRI time courses for subthreshold block-design stimulation from the ipsilateral hippocampus averaged across subjects. (FIG. 5, panel d) Average LFP band power change from baseline (calculated over each 3 second period) for subthreshold stimulation in the Beta and Theta and Alpha bands. (Error-bars are shown as ±S.E.M.). (FIG. 5, panel e) fMRI time courses from the ipsi- and contralateral hippocampi and septum during optogenetically-induced afterdischarges (averaged across subjects). (FIG. 5, panel f) Average LFP band power change from baseline for the supra threshold stimulation in the Beta and Theta and Alpha bands (Error-bars are shown as ±S.E.M.). (FIG. 5, panel g) Segmentation of MRI images into different brain regions. Segmented regions were overlaid as colored ROIs on a structural (FSE) MRI image. (FIG. 5, panel h) Scatter/bar graph showing percentage of significantly activated voxels within a ROI vs. Region of interest for both subthreshold stimulations and seizure-like afterdischarges. Bars indicate the mean value across all 5 subjects and error bars represent ±S.E.M. Significantly activated voxels were considered to be those with a p-value of <0.01, voxel-wise FDR corrected. All panels include n=5 rats. Abbreviations: Acb—Accumbens Nucleus, Amyg—Amygdala, Cpu—Caudate Putamen, M—Motor Cortex, RS—Retrosplenial Cortex, Thal DL—

Thalamus Dorsal-Lateral, Thal VM—Thalamus Ventral-Medial, Cg—Cingulate Cortex, Ent—Entorhinal Cortex, HF—Hippocampal Formation, S1—Primary Somatosensory Cortex, Sep—Septum.

Figure 6:
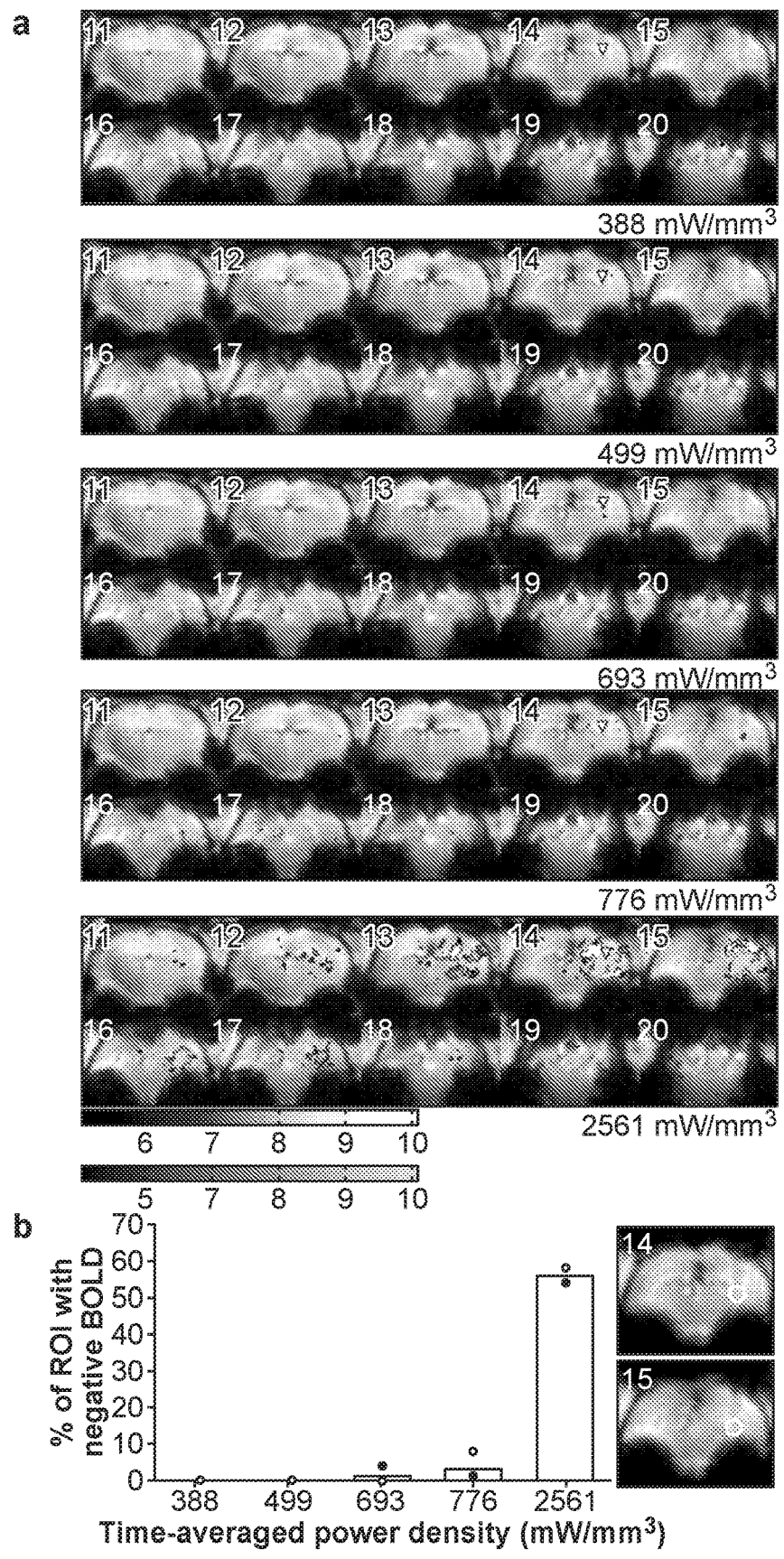

FIG. 6: ofMRI at different time-averaged light power densities in control (saline injected) rats not expressing ChR2, according to embodiments of the present disclosure. (FIG. 6, panel a) T-statistic maps showing regions of significant positive and negative fMRI signal changes at different light power densities (388-2561 mW/mm$^3$). For power levels 388-776 mW/mm$^3$, stimulation paradigms included 20 s trains of 20 Hz, 15 ms pulse duration (30% duty cycle), whereas for the 2561 mW/mm$^3$ level, a 99% duty cycle was used at 10 Hz. (FIG. 6, panel b) Bar graph displaying mean percentage of ROI exhibiting significant negative fMRI signal change at different power levels (n=3 for 388-776 mW/mm$^3$ and n=2 for 2561 mW/mm$^3$). Quantification was performed using a circular ROI placed below the optrode and included 7 voxels in diameter across 2 consecutive slices (right panel). Site of optical stimulation is marked by an inverted triangle. T-statistic maps were thresholded at a significance level of p<0.01, voxel-wise FDR corrected. These data indicated that the time-averaged light-intensity range used for ofMRI experiments (56-167 mW/mm$^2$) was far below the range that generates artifactual responses.

DEFINITIONS

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product," depending on the context.

The term "genetic modification" refers to a permanent or transient genetic change induced in a cell following introduction into the cell of a heterologous nucleic acid (i.e., nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The terms "light-activated," "light-responsive" in reference to a polypeptide or protein that is light-responsive, are used interchangeably and include light-responsive ion channels or opsins, and ion pumps as described herein. Such light-responsive proteins may have a depolarizing or hyperpolarizing effect on the cell on whose plasma membrane the protein is expressed depending on the ion permeability of the activated protein, and the electrochemical gradients present across the plasma membrane.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Excitable cell," as used herein, refers to electrically excitable cells, such as neurons and muscle cells. Excitable cells typically use changes in their membrane potential to transmit signals within the cell. Thus, an excitable cell may be characterized in having a resting state, where the membrane potential is at the resting membrane potential, and an excited state, where rapid depolarization of the membrane potential is transmitted across the cell as an action potential. The "cellular electrical activity" of an excitable cell may refer to the changes in the membrane potential or may refer to any indirect measure of the changes in membrane potential, such as the changes in intracellular calcium concentration or any other biochemical changes that is a functional measure of the change in the membrane potential.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an opsin" includes a plurality of such opsins and reference to "the carbon fiber" includes reference to one or more carbon fibers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a device for carrying out magnetic resonance imaging compatible optogenetics; and methods for using the device. Aspects of the embodiments of the devices are described in more detail in the following section. In addition, embodiments of the methods of using the devices are also described herein.

Devices

The present disclosure provides an implantable device that includes an optrode. Certain embodiments of the subject optrodes include a carbon fiber electrode. A carbon fiber electrode is an electrode composed of carbon fiber (e.g., carbon fiber filaments) that conducts electricity. As such, a carbon fiber electrode can be used to detect electrical signals (and/or changes in electrical signals), such as electrical signals produced near the carbon fiber electrode during use. In some cases, the carbon fiber electrode is configured to detect an electrical signal, such as a local field potential (LFP). An LFP is an electrophysiological signal (electrical potential, or voltage) generated by the summed electric current flowing from multiple nearby neurons within a localized volume of nervous tissue. Voltage is produced across the local extracellular space by action potentials and graded potentials in neurons in the area, and can vary as a result of synaptic activity. For instance, the subject optrode, e.g., the carbon fiber electrode of the optrode, can detect cellular electrical activity of an excitable cell, such as neurons and muscle cells.

In some cases, the optrode is adapted for use in magnetic resonance imaging (MRI). As such, optrodes of the present disclosure are configured to produce less artifacts in images obtained using MRI as compared to conventional electrodes, such as conventional metal electrodes (e.g., tungsten wire electrodes). As discussed herein, optrodes of the present disclosure include a carbon fiber electrode rather than a metal wire electrode, which facilitates a reduction and/or elimination of artifacts in MRI using the optrodes of the present disclosure.

In certain embodiments, the carbon fiber electrode includes carbon fibers (carbon filaments). The carbon fiber electrode may include a plurality of carbon fibers. In some cases, the carbon fibers are bundled together to form the carbon fiber electrode. As such, the carbon fiber electrode may include a bundle of carbon fibers. The carbon fiber electrode may include 10 or more carbon fibers bundled together to form the carbon fiber electrode, such as 50 or more carbon fibers, or 100 or more, or 200 or more, or 250 or more, or 300 or more, or 400 or more, or 500 or more, or 600 or more, or 700 or more, or 750 or more, or 800 or more, or 900 or more, or 1000 or more carbon fibers bundled together to form the carbon fiber electrode. In some instances, the carbon fiber electrode includes 1000 or less carbon fibers bundled together to form the carbon fiber electrode, such as 900 or less carbon fibers, or 800 or less, or 750 or less, or 700 or less, or 600 or less, or 500 or less, or 400 or less, or 300 or less, or 250 or less, or 200 or less, or 100 or less, or 50 or less, or 10 or less carbon fibers bundled together to form the carbon fiber electrode. Accordingly, the carbon fiber electrode may include from 10 to 1000 carbon fibers bundled together to form the carbon fiber electrode, such as from 100 to 900 carbon fibers, or from 200 to 800 carbon fibers. Other embodiments of the carbon fiber electrode may include from 100 to 500 carbon fibers, or from 100 to 400 carbon fibers, or from 100 to 300 carbon fibers, or from 200 to 300 carbon fibers bundled together to form the carbon fiber electrode. Other embodiments of the carbon fiber electrode may include from 500 to 900 carbon fibers, or from 500 to 800 carbon fibers, or from 600 to 800 carbon fibers, or from 700 to 800 carbon fibers bundled together to form the carbon fiber electrode. For example, the carbon fiber electrode may include 1000 carbon fibers bundled together to form the carbon fiber electrode. In some cases, the carbon fiber electrode includes 750 carbon fibers bundled together to form the carbon fiber electrode. In other cases, the carbon fiber electrode includes 250 carbon fibers bundled together to form the carbon fiber electrode.

In certain embodiments, the carbon fiber electrode has a diameter of from 10 µm to 300 µm, such as from 25 µm to 300 µm, or from 50 µm to 300 µm, or from 75 µm to 300 µm, or from 75 µm to 275 µm, or from 75 µm to 250 µm, or from 75 µm to 225 µm, or from 75 µm to 200 µm, or from 100 µm to 200 µm, or from 125 µm to 200 µm, or from 125 µm to 175 µm. Diameters between any of the values of these ranges are also possible, such as a carbon fiber electrode having a diameter of from 10 µm to 200 µm, such as from 10 µm to 190 µm, or from 10 µm to 180 µm, or from 25 µm to 180 µm, or from 50 µm to 180 µm, or from 75 µm to 180 µm, or from 100 µm to 180 µm, or from 110 µm to 180 µm, or from 120 µm to 180 µm, or from 125 µm to 180 µm, or from 125 µm to 175 µm. In some cases, the carbon fiber electrode has a diameter of from 270 µm to 295 µm, such as from 275 µm to 290 µm. For example, the carbon fiber electrode may have a diameter of about 280 µm. In some cases, the carbon fiber electrode has a diameter of from 155 µm to 190 µm, such as from 160 µm to 180 µm, or from 165 µm to 175 µm. For example, the carbon fiber electrode may have a diameter of about 170 µm. In some cases, the carbon fiber electrode has a diameter of from 100 µm to 150 µm, such as from 120 µm to 140 µm, or from 125 µm to 140 µm. For example, the carbon fiber electrode may have a diameter of about 130 µm. By "diameter" is meant the mean diameter.

In certain embodiments, the carbon fiber electrode includes an insulation coating. The insulation coating may be configured to insulate the carbon fiber electrode from electrical signals. For example, the insulation coating may be configured to substantially block the transmission of electrical signals from the surrounding environment to the carbon fiber electrode. In some cases, a bundle of carbon fibers that make up the carbon fiber electrode may be held (bundled) together by the insulation coating.

In general, optrodes of the present disclosure are composed of a biocompatible material. Biocompatible materials suitable for use in embodiments of the present devices include materials that do not substantially react with surrounding tissue and/or fluids of the subject in which the device is implanted. Biocompatible materials include materials that are substantially non-antigenic when placed on or in living tissue for an extended period of time. For example, biocompatible materials may include materials that can be placed on or in living tissue for an extended period of time, such as for a period of 2 days or more, such as 1 week or more, 4 weeks or more, 6 months or more, or 1 year or more, e.g., 5 years or more, up to and including the remaining lifetime or expected remaining lifetime of the subject or more, and not cause a significant adverse (e.g., detrimental to health) reaction (e.g., an immune response) in the tissue or the associated organism. Thus, devices of the present disclosure may be implantable devices, where at least a portion of the device (e.g., at least a portion of the optrode) is configured to be implantable for an extended period of time in a subject as discussed above.

Biocompatible materials, as included in the subject devices, can include any suitable biocompatible material. Biocompatible materials of the subject devices, in some instances, are polymeric materials (e.g., materials having one or more polymers including, for example, plastic and/or rubber) and/or metallic materials. Such materials may have characteristics of flexibility and/or high strength (e.g., able to withstand significant force, such as a force exerted on it by a tissue within a human body, without breaking and/or resistant to wear) and/or high fatigue resistance (e.g., able to retain its physical properties for long periods of time regardless of the amount of use or environment).

As noted above, any of the components of the described devices may be composed of a variety of materials. Such materials may be flexible materials and some materials may be rigid materials. By "flexible", as used herein is meant pliable or capable of being bent or flexed repeatedly (e.g., bent or flexed with a force exerted by a human hand or other body part) without damage (e.g., physical deterioration). A flexible material may be a material that remains able to perform intended function (e.g., repeatedly flexing) by remaining pliable for at least the expected lifetime or useful lifetime of the component which the material is included in.

In some embodiments, the insulation coating on the exterior surface of the carbon fiber electrode is the layer of material that comes into contact with the surrounding tissues and/or fluids in the subject during use. As such, the insulation coating may be composed of a biocompatible material as described above. In addition, the insulation coating may be a flexible material as described above. Materials of interest for the insulation coating may include any suitable biocompatible material, such as a biocompatible polymeric material. For instance, suitable insulation coating materials may include, but are not limited to: polymeric materials, such as polyvinylidene fluoride or polyvinylidene difluoride (PVDF), polydimethylsiloxane (PDMS), polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, and the like, and combinations thereof. In some cases, the insulation coating is composed of PVDF. In some cases, the insulation coating is composed of PDMS.

The insulation coating may include one or more layers of an insulation material coated onto an exterior surface of the carbon fiber electrode. In some cases, each layer of the insulation coating is composed of the same insulation material. In other embodiments, the layers of the insulation coating may be composed of different insulation materials. In some instances, substantially the entire exterior surface of the carbon fiber electrode is coated by the insulation coating. In some cases, a portion of the carbon fiber electrode, such as the distal end (distal tip) of the carbon fiber electrode, is uninsulated; e.g., the distal end of the carbon fiber electrode does not have an insulation coating. By "distal" is meant a portion or end of a component that is further away from the operator (i.e., closer to the subject) during use. In certain cases, an uninsulated distal end of the carbon fiber electrode allows the carbon fiber electrode to detect electrical signals produced near its distal end during use. For example, the carbon fiber electrode can detect cellular electrical activity of excitable cell or cells in a target area, e.g., adjacent the uninsulated distal end of the carbon fiber electrode. In some instances, the insulation coating on the carbon fiber electrode shields the carbon fiber electrode from detection of electrical signals produced in surrounding areas that are outside of the target area. In this manner, the insulation coating may prevent or reduce extraneous background signals from significantly interfering with the detected signal.

In certain embodiments, the carbon fiber electrode is attached to a conductor. For example, the carbon fiber electrode may be attached to a wire or conductor, such as a metal wire or a metal conductor. The carbon fiber electrode may be attached such that the carbon fiber electrode is electrically connected to the conductor (e.g., metal wire or metal conductor). Signals acquired by the carbon fiber electrode thus may be transmitted from the carbon fiber electrode to the conductor, e.g., for transmission of the signals to a detector and/or processor for subsequent analysis. Metals useful for the conductor (e.g., metal wire or metal conductor) include any suitable electrically conductive metal, such as, but not limited to, copper, silver, gold, aluminum, brass, nickel, tungsten, and the like, and combinations thereof. In some instances, the carbon fiber electrode is attached to the conductor at the proximal end of the carbon fiber electrode. By "proximal" is meant a portion or end of a component that is closer to the operator (i.e., further away from the subject) during use. As such, the distal end of the conductor may be attached to the proximal end of the carbon fiber electrode. In some cases, the carbon fiber electrode is attached to the conductor at the proximal end of the carbon fiber electrode such that the carbon fiber electrode itself does not contain the conductor. For instance, at least a portion of the carbon fiber electrode (e.g., the portion of the carbon fiber electrode inserted into the subject during use) does not include the conductor (e.g., the metal wire or metal conductor). A carbon fiber electrode that does not include the conductor as described above may facilitate a reduction or minimization in artifacts in MRI (e.g., fMRI) during use.

The carbon fiber electrode may be attached to the conductor with an adhesive, such as a conductive adhesive. The conductive adhesive may be an electrically conductive adhesive, such that a stable electrical connection is maintained between the carbon fiber electrode and the conductor during use. Examples of suitable conductive adhesives include, but are not limited to, a conductive silver epoxy, a conductive graphite epoxy, a conductive nickel epoxy, and the like, and combinations thereof. In certain cases, the conductive adhesive is a conductive silver epoxy adhesive.

A device of the present disclosure, when used in carrying out MRI (e.g., functional MRI), exhibits lower impedance as compared to a device in which the optrode is made from conventional materials, such as a 50 μm diameter tungsten wire. For example, the impedance may be 10% or more, 20% or more, 30% or more, 40% or more, or 50% or more less than a device in which the optrode is made from conventional materials, such as with a 50 μm diameter tungsten wire. In some embodiments, the carbon fiber electrode has an impedance magnitude of 500 kΩ or less, such as 450 kΩ or less, or 400 kΩ or less, or 350 kΩ or less, or 300 kΩ or less, or 250 kΩ or less, or 200 kΩ or less, or 175 kΩ or less, or 150 kΩ or less, or 125 kΩ or less, or 100 kΩ or less, or 90 kΩ or less, or 80 kΩ or less, or 70 kΩ or less, or 60 kΩ or less, or 50 kΩ or less, or 40 kΩ or less, or 30 kΩ or less, or 20 kΩ or less, or 10 kΩ or less, or 5 kΩ or less. In some cases, the carbon fiber electrode has an impedance magnitude of 30 kΩ or less, e.g., about 30 kΩ. In some cases, the carbon fiber electrode has an impedance magnitude of 50 kΩ or less, e.g., about 50 kΩ. In some cases, the carbon fiber electrode has an impedance magnitude of 80 kΩ or less, e.g., about 80 kΩ. In some cases, the carbon fiber electrode has an impedance magnitude of 200 kΩ or less. For instance, the carbon fiber electrode may have an impedance magnitude ranging from 10 kΩ to 500 kΩ, such as from 10 kΩ to 400 kΩ, or from 10 kΩ to 300 kΩ, or from 10 kΩ to 200 kΩ, or from 10 kΩ to 150 kΩ, or from 10 kΩ to 100 kΩ, or from 10 kΩ to 90 kΩ, or from 10 kΩ to 80 kΩ, or from 20 kΩ to 80 kΩ. In some cases, the carbon fiber electrode has an impedance magnitude ranging from 10 kΩ to 100 kΩ, such as from 20 kΩ to 80 kΩ, or from 40 kΩ to 80 kΩ. For example, the carbon fiber electrode may have an impedance magnitude ranging from 20 kΩ to 30 kΩ. In some cases, the carbon fiber electrode has an impedance magnitude ranging from 40 kΩ to 50 kΩ. In some cases, the carbon fiber electrode has an impedance magnitude ranging from 75 kΩ to 85 kΩ. The impedance values described herein can be obtained at 100 Hz in 0.9% (w/v) sodium chloride in water.

In certain embodiments, the carbon fiber electrode is configured for uniplex analysis of a target area (e.g., target tissue or organ) in a subject. By "uniplex analysis" is meant that a single target area is analyzed using the devices and methods disclosed herein. For example, a single carbon fiber electrode may be included in the optrode for analysis of one target area in a subject. In these embodiments, the optrode is configured for detection and analysis of single-unit activity in a subject.

Other embodiments include the multiplex analysis of two or more target areas (e.g., target tissues or organs) in a subject. By "multiplex analysis" is meant that the two or more areas of excitable cells may be analyzed using the devices and methods disclosed herein. For example, the optrode may include two or more carbon fiber electrodes. Each carbon fiber electrode in the optrode may be a carbon fiber electrode as described herein. In some cases, each carbon fiber electrode in the optrode includes its own insulation coating as described herein. Individual carbon fiber electrode each with their own insulation coating may facilitate detection of electrical signals from different target areas while minimizing cross-talk between the carbon fiber electrodes. In some instances, the number of target areas for analysis using multiplex devices as disclosed herein is 2 or more, such as 4 or more, 6 or more, 8 or more, 10 or more, etc., up to 20 or more, e.g., 50 or more, including 100 or more, or 500 or more distinct target areas. In certain embodiments, the devices and methods may be used for the multiplex analysis of 2 to 500 distinct target areas in the subject, such as 2 to 250 distinct target areas, including 2 to 100 distinct target areas, or 2 to 50 distinct target areas, or 2 to 25 distinct target areas, or 2 to 10 distinct target areas. In certain embodiments, 2 or more multiplex assays may be conducted in parallel substantially simultaneously.

As discussed above, the device of the present disclosure may be configured for multiplex analysis, such that the optrode is configured for detection and analysis of multi-unit activity in a subject. As such, the optrode may be configured to include an array of carbon fiber electrodes. An "array" includes any arrangement of individually addressable carbon fiber electrodes. An array is "addressable" when it has multiple carbon fiber electrodes and each carbon fiber electrode may carry a signal independent of the other carbon fiber electrodes in the array. Thus, an array of carbon fiber electrodes may be used to detect distinct signals from different target tissues or organs in a subject. An array may contain 2 or more, 4 or more, 8 or more, 10 or more, 50 or more, 100 or more, 250 or more, or 500 or more carbon fiber electrodes. As discussed above, each carbon fiber electrode in the array may be individually insulated.

In certain embodiments, the optrode includes a reference electrode. The reference electrode may be configured to detect a reference or background signal from the assay environment surrounding the optrode or from the subject being tested, such as from the cerebellum of the subject bring tested. The signals obtained from the reference electrode may be compared to the signals obtained from the carbon fiber electrode during analysis of the acquired data. The reference electrode may be composed of any convenient conductive material, such as, for example, a conductive metal, e.g, copper, silver, gold, aluminum, brass, nickel, tungsten, and the like, and combinations thereof. In some cases, the reference electrode is a brass electrode. The reference electrode may be attached (e.g., electrically connected) to a conductor, such as a metal wire as described above.

In certain embodiments, the carbon fiber electrode and/or the reference electrode are connected to a detector and/or a processor. The detector may detect the signals acquired by the carbon fiber electrode and/or the reference electrode. The processor (e.g., a signal processor) may be configured to analyze the detected signals and/or save the detected signals and results of the signal analysis. In some cases, the processor is configured to analyze the signals in real-time. By "real-time" is meant that the acquired signals are analyzed by the processor immediately after signal acquisition. In other cases, the acquired signals are saved by the processor in a memory for subsequent analysis of the data.

Embodiments of the device may also include a light source. In some cases, the light source includes an optical fiber. The optical fiber may be configured to direct light to a target area (e.g., a target tissue or organ) in a subject. For example, the optical fiber may direct light to a target area in the subject that contains excitable cells, such as neurons or muscle cells. As discussed in more detail below, the excitable cells (e.g., neurons) in a target tissue or organ may be genetically modified to express a light-responsive polypeptide that, when stimulated by an appropriate light stimulus, hyperpolarizes or depolarizes the stimulated excitable cell. Thus, the optical fiber may be used to direct light to the target tissue or organ to stimulate the excitable cells. As discussed herein, the carbon fiber electrode may be used to detect electrical signals and/or changes in electrical signals produced by the excitable cells. In some cases, the distal end of the optical fiber is positioned adjacent to the target area in the subject. Light emitted from the distal end of the optical fiber may stimulate the excitable cells as discussed herein. In certain instances, the proximal end of the optical fiber is attached to a source of light. The source of light may be any source of light suitable for performing a desired assay, such as, for example, a source of light that produces light of an appropriate wavelength to stimulate the excitable cells in the target area of the subject. In some cases, the light source is a laser. In some cases, the light source is a light emitting diode (LED). In some cases, two or more light sources may be included in the device, such as light sources that produce light of different wavelengths. In some cases, the device also includes an optical switch.

The optical fiber of the optrode may be associated with the carbon fiber electrode. In some cases, the optical fiber is attached to the carbon fiber electrode. For example, an adhesive may be used to attach the optical fiber to the carbon fiber electrode. In certain instances, the distal tip of the optical fiber and the distal tip of the carbon fiber electrode are positioned adjacent each other when the optical fiber and the carbon fiber electrode are attached to each other. In some cases, the distal end of the optical fiber and the distal end of the carbon fiber electrode are aligned parallel to each other. In some cases, the ends of the optical fiber and the carbon fiber electrode are aligned such that neither end extends further distally than the other. An optrode having the distal end of the optical fiber aligned with the distal end of the carbon fiber electrode may facilitate signal acquisition by the carbon fiber electrode at the same target area in the subject that is stimulated by the optical fiber.

In certain instances, the implantable device of the present disclosure is provided in a sterile condition. For example, the device or a at least a portion thereof (e.g., the optrode) may be provided in a sterile packaging. A sterile packaging is configured to maintain the device enclosed in the packaging in a sterile environment. By "sterile" is meant that there are substantially no microbes (such as fungi, bacteria, viruses, spore forms, etc.).

Methods

The present disclosure provides a method for monitoring activity in an excitable organ or tissue of an individual (also referred to as "a subject" herein). In certain embodiments, the method includes surgically implanting a device of the present disclosure into or adjacent to an organ or tissue of an individual, and monitoring the activity of the organ or tissue. In some cases, surgically implanting the device includes opening an access in the subject and inserting at least a portion of the device through the access. The access may be an access through the skin, bone, muscle, and/or other tissues of the subject. For instance, an access may include an access through bone (e.g., skull) of the subject to allow placement of at least a portion of the device (e.g., the optrode) adjacent to target neurons in the subject.

As indicated above, embodiments of the method include monitoring the activity of the organ or tissue. In some instances, monitoring the activity of the organ or tissue includes conducting functional magnetic resonance imaging (fMRI) on the organ or tissue. In some cases, the organ or tissue includes excitable cells (e.g., cells that express one or more light-responsive polypeptides). In some cases, the one or more light-responsive polypeptides include a hyperpolarizing light-responsive polypeptide. In some cases, the one or more light-responsive polypeptides include a depolarizing light-responsive polypeptide. As such, in some cases the method includes producing an image of the target organ or tissue using fMRI. In some cases, fMRI may be used to image the organ or tissue prior to delivering light to the target organ or tissue using the optrode. In some cases, fMRI may be used to image the organ or tissue during delivery of light to the target organ or tissue using the optrode. In some cases, fMRI may be used to image the organ or tissue after delivering light to the target organ or tissue using the optrode.

The method may further include detecting and/or recording a detectable parameter of the organ or tissue using the device (e.g., optrode). As discussed herein, the optrode may include a carbon fiber electrode configured to detect electrical signals, such as local field potentials produced by changes in the membrane potential of the excitable cells. Thus, in some cases, the method includes detecting and/or recording a detectable parameter of the organ or tissue using a carbon fiber electrode of the optrode.

As described herein, the device (e.g., optrode) may include a light source. In these embodiments, the method includes delivering light to the target organ or tissue using the light source. For instance, the method may include stimulating the excitable cells in the target organ or tissue with light from the light source. In some cases, the light source includes an optical fiber as described herein. As such, in these embodiments, the method includes delivering light to the target organ or tissue using the optical fiber (e.g., stimulating the excitable cells with light delivered by the optical fiber). In some cases, the light source includes a laser. As such, in some embodiments, the method includes delivering light to the target organ or tissue using the laser. For example, the method may include generating light using the laser and directing the light from the laser to the target organ or tissue using the optical fiber (e.g., for stimulating the excitable cells in the target organ or tissue with light from the laser). In some cases, the light source includes a light-emitting diode (LED). As such, in some embodiments, the method includes delivering light to the target organ or tissue using the LED. For instance, the method may include generating light using the LED and directing the light from the LED to the target organ or tissue using the optical fiber (e.g., for stimulating the excitable cells in the target organ or tissue with light from the LED).

In certain embodiments, the detectable parameter of the target organ or tissue includes local field potentials, e.g., local field potentials produced by changes in the membrane potential of the excitable cells. As discussed in more detail below, the local field potentials may be produced by stimulating the excitable cells with light from the light source. In some instances, the detectable parameter is a single-unit activity, e.g., detectable activity from a single target area (i.e., a uniplex assay). In some cases, the detectable parameter is a multi-unit activity, e.g., detectable activity from two or more target areas (i.e., a multiplex assay).

In some instances, monitoring the activity of the organ or tissue is performed once. In other cases, monitoring the activity of the organ or tissue is performed two or more times. In some cases, monitoring the activity of the organ or tissue is performed several times over a period of time, e.g., the method includes chronically monitoring the activity of the organ or tissue. In some cases, monitoring the activity of the organ or tissue may be performed over an extended period of time, such as 1 day or more, 2 days or more, 3 days or more, 4 days or more, 5 days or more, 6 days or more, 7 days or more, 8 days or more, 9 days or more, 10 days or more, such as, for example, 1 week or more, 2 weeks or more, 3 weeks or more, 1 month or more, 2 months or more, 3 months or more, 4 months or more, 5 months or more, 6 months or more, 7 months or more, 8 months or more, 9 months or more, 10 months or more, 11 months or more, 1 year or more, or ever longer periods of time.

In some cases, the individual is a human. In some cases, the individual is a non-human primate. In some cases, the individual is a rodent (e.g., a rat, a mouse, etc.). The tissue or organ (e.g., "target tissue" or "target organ") may be an in vivo neuronal tissue, a tissue slice preparation, a nerve fiber bundle, a neuromuscular junction, etc. The in vivo neuronal tissue may be neuronal tissue of an animal that is anesthetized or non-anesthetized, and is restrained or non-restrained. The target tissue of interest includes, but is not limited to, the neocortex, the hypothalamus, entorhinal and hippocampal formation cortex, mammillary bodies, septum, bed nucleus of stria terminalis, dorsal and ventral striatum, thalamus, amygdala, accumbens, brainstem, subcortical structures in general, muscle, spinal cord, cardiac tissue, etc.

In some embodiments, the excitable cells (e.g., neurons) in a target tissue or organ are genetically modified to express a light-responsive polypeptide that, when stimulated by an appropriate light stimulus, hyperpolarizes or depolarizes the stimulated excitable cell. In some instances, the light-responsive polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the excitable cell when activated by light of an activating wavelength. In some embodiments, the light-responsive polypeptide hyperpolarizes the excitable cell when activated by light of an activating wavelength.

In some embodiments, the light-responsive polypeptides are activated by blue light. In some embodiments, the light-responsive polypeptides are activated by green light. In some embodiments, the light-responsive polypeptides are activated by yellow light. In some embodiments, the light-responsive polypeptides are activated by orange light. In some embodiments, the light-responsive polypeptides are activated by red light.

In some embodiments, the light-responsive polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive polypeptide. In some cases, the one or more amino acid sequence motifs which enhance light-responsive polypeptide transport to the plasma membranes of mammalian cells is fused internally within a light-responsive polypeptide. Optionally, the light-responsive polypeptide and the one or more amino acid sequence motifs may be separated by a linker. In some embodiments, the light-responsive polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In some embodiments, the signal peptide sequence in the protein can be deleted or substituted with a signal peptide sequence from a different protein.

Exemplary light-responsive polypeptides and amino acid sequence motifs that find use in the present system and method are disclosed in, e.g., PCT App. Nos. PCT/US2011/028893 and PCT/US2015/23087. Representative light-responsive polypeptides that find use in the present disclosure are further described below.

In some embodiments, a depolarizing light-responsive polypeptide is a channelrhodopsin (ChR1—NCBI Gene ID: 5724518, ChR2—NCBI Gene ID: 5727376) derived from *Chlamydomonas reinhardtii*, wherein the polypeptide is capable of transporting cations across a cell membrane when the cell is illuminated with light. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization of the excitable cells, e.g., neurons, expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane.

In other embodiments, the light-responsive polypeptide is a step function opsin (SFO) protein or a stabilized step function opsin (SSFO) protein that can have specific amino acid substitutions at key positions in the retinal binding pocket of the amino acid sequence of ChR2. Further disclosure related to SFO or SSFO proteins can be found in International Patent Application Publication No. WO 2010/056970, the disclosure of which is hereby incorporated by reference in its entirety.

In some embodiments, a suitable light-responsive polypeptide is a cation channel derived from *Volvox carteri* (VChR1—NCBI Gene ID: 9619570) and is activated by illumination with light of a wavelength of from about 500 nm to about 600 nm, e.g., from about 525 nm to about 550 nm, e.g., 545 nm. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can comprise one or more conservative amino acid substitutions and/or one or more non-conservative amino acid substitutions. The light-responsive ion channel protein containing substitutions, deletions, and/or insertions introduced into the native amino acid sequence suitably retains the ability to transport ions across the plasma membrane of a excitable cell in response to light.

In other embodiments, the light-responsive polypeptide is a SFO or an SSFO based on VChR1. In some embodiments an SFO or SSFO protein is capable of mediating a depolarizing current in the cell when the cell is illuminated with blue light. In some embodiments, the light has a wavelength of about 560 nm. Additionally, in some embodiments the light is delivered as a single pulse of light or as spaced pulses of light due to the prolonged stability of SFO and SSFO photocurrents. In some embodiments, activation of the SFO or SSFO protein with single pulses or spaced pulses of light can cause depolarization of an excitable cell, e.g., neuron, expressing the SFO or SSFO protein. In some embodiments, each of the disclosed step function opsin and stabilized step function opsin proteins can have specific properties and characteristics for use in depolarizing the membrane of an excitable cell in response to light.

In other embodiments, the light-responsive cation channel protein is a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1.

In some embodiments, the C1V1 protein mediates a depolarizing current in the cell when the cell is illuminated with green light. In some embodiments, the light has a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, suitable light-responsive proteins include C1V1 chimeric light-responsive proteins that can have specific amino acid substitutions at key positions throughout the retinal binding pocket of the VChR1 portion of the chimeric polypeptide.

In other embodiments, the light-responsive cation channel protein is a C1C2 chimeric protein derived from the ChR1 and the ChR2 proteins from *Chlamydomonas reinhardti*, wherein the protein is responsive to light and is capable of mediating a depolarizing current in the cell when the cell is illuminated with light. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein comprises one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane.

In some aspects, a depolarizing light-responsive polypeptide is a red shifted variant of a depolarizing light-responsive polypeptide derived from *Chlamydomonas reinhardtii*; such light-responsive polypeptides are referred to herein as a "ReaChR polypeptide" or "ReaChR protein" or "ReaChR."

The light used to activate the ReaChR polypeptide can have a wavelength between about 590 and about 630 nm or can have a wavelength of about 610 nm. The ReaChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the ReaChR protein can comprise one or more conservative amino acid substitutions and/or one or more non-conservative amino acid substitutions. The ReaChR containing substitutions, deletions, and/or insertions introduced into the native amino acid sequence suitably retains the ability to transport cations across a cell membrane.

In some aspects, a depolarizing light-responsive polypeptide is a SdChR polypeptide (Genbank Accession No.: AHH02138) derived from *Scherffelia dubia*, wherein the SdChR polypeptide is capable of transporting cations across a cell membrane when the cell is illuminated with light. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane.

In some aspects, a depolarizing light-responsive polypeptide can be, e.g. CnChR2 (Genbank Accession No.: AHH02139), derived from *Chlamydomonas noctigama*, wherein the CnChR1 polypeptide is capable of transporting cations across a cell membrane when the cell is illuminated with light. The light used to activate the CnChR1 polypeptide can have a wavelength between about 560 and about 630 nm or can have a wavelength of about 600 nm. The CnChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR1 protein to regulate the polarization state of the plasma membrane of the cell. In some cases, the CnChR1 protein comprises one or more conservative amino acid substitutions and/or one or more non-conservative amino acid substitutions. The CnChR1 protein containing substitutions, deletions, and/or insertions introduced into the native amino acid sequence suitably retains the ability to transport cations across a cell membrane.

In other embodiments, the light-responsive cation channel protein is a CsChrimson chimeric protein derived from a CsChR (Genbank Accession No.: AHH02144) protein of *Chloromonas subdivisa* and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell. Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane.

In some aspects, a depolarizing light-responsive polypeptide can be, e.g. ShChR1 (Genbank Accession No.: AHH02106), derived from *Stigeoclonium helveticum*, wherein the ShChR1 polypeptide is capable of transporting cations across a cell membrane when the cell is illuminated with light. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane.

In some embodiments, a suitable hyperpolarizing light-responsive polypeptide is an Archaerhodopsin (Arch—Genbank Accession No.: ADB03111) proton pump (e.g., a proton pump derived from *Halorubrum sodomense*) that can transport one or more protons across the plasma membrane of a cell when the cell is illuminated with light. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a target cell in response to light.

In some embodiments, a suitable light-activated protein is an Archaerhodopsin (ArchT—Genbank Accession No.: ABT17417) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a target cell in response to light.

In some embodiments, the light-responsive polypeptide is responsive to blue light and is a proton pump protein derived from *Guillardia theta*, wherein the proton pump protein is capable of mediating a hyperpolarizing current in the cell when the cell is illuminated with blue light; such a protein is referred to herein as a "GtR3 protein" or a "GtR3 polypeptide". The GtR3 (NCBI Gene ID: 17301498) protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of an excitable cell, e.g., neuron, in response to light.

In some embodiments, a light-activated protein is an *Oxyrrhis marina* (Oxy—Genbank Accession No.: ADY17806) proton pump that can transport one or more protons across the plasma membrane of a cell when the cell is illuminated with light. The light can have a wavelength between about 500 and about 560 nm or can have a wavelength of about 530 nm. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a target cell in response to light.

In some embodiments, the light-responsive proton pump protein (referred to herein as "Mac protein"—NCBI Gene ID: 13287905) is responsive to light and is derived from *Leptosphaeria maculans*, wherein the Mac proton pump protein is capable of pumping protons across the membrane of a cell when the cell is illuminated with 520 nm to 560 nm light. The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of an excitable cell, e.g., neuron, in response to light.

In some cases, a suitable light-responsive chloride pump protein is derived from *Natronomonas pharaonis*; such a protein is referred to herein as an "NpHR protein" or an "NpHR polypeptide." In some embodiments, the NpHR (NCBI Gene ID: 3702828) protein can be responsive to amber light as well as red light and can mediate a hyperpolarizing current in the excitable cell, e.g., the neuron, when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. A NpHR protein containing substitutions, deletions, and/or insertions introduced into the native amino acid sequence suitably retains the ability to hyperpolarize the plasma membrane of an excitable cell in response to light.

Further disclosure related to light-responsive chloride pump proteins can be found in U.S. Patent Application Publication Nos.: 2009/0093403 and 2010/0145418, as well as in International Patent Application No.: PCT/US2011/028893, the disclosures of each of which are hereby incorporated by reference in their entireties.

In some embodiments, a suitable light-responsive ion channel protein is, e.g., a DsChR protein (Genbank Accession No.: AEY68833) derived from *Dunaliella salina*, wherein the ion channel protein is capable of mediating a hyperpolarizing current in the cell when the cell is illuminated with light. The light can have a wavelength between about 470 nm and about 510 nm or can have a wavelength of about 490 nm. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of an excitable cell, e.g., a neuron, in response to light.

In some embodiments, a hyperpolarizing light-responsive ion channel is based on a depolarizing light-responsive ion channel, as described in, e.g., PCT App. No. PCT/US2015/23087, which is incorporated herein by reference. In some embodiments, a light-responsive anion channel polypeptide is based on a C1C2 protein (Genbank Accession No.:

AHA49646). In some embodiments, a suitable hyperpolarizing light-responsive polypeptide is based on the amino acid sequence of the protein ChR2 (Genbank Accession No.: AER29835). In some embodiments, a suitable hyperpolarizing light-responsive polypeptide is based on the amino acid sequence of the protein C1V1 (Genbank Accession No.: AEL28924). In some embodiments, a subject hyperpolarizing light-responsive polypeptide is based on the amino acid sequence of the protein ReaChR (Genbank Accession No.: AGT48260).

Also provided herein is a light-responsive polypeptide encoded in a nucleic acid, e.g., encoded as part of an expression vector. In such instances, the excitable cells, e.g., neurons, may be genetically modified with the nucleic acid to adapt the excitable cells to hyperpolarize and/or depolarize in response to a light stimulus. Any suitable nucleic acid and expression vector may be used to encode the light-responsive polypeptide.

In some embodiments, a portion of a nucleic acid encoding a light-responsive polypeptide is operably linked to a promoter sequence. Any suitable promoter that functions in the excitable cell of interest in the target tissue can be used for expression of the subject nucleic acids. In certain embodiments, a promoter sequence can be a promoter that is specific to a particular target cell type or to a particular tissue type, such as a particular excitable cell, a particular muscle cell, a particular neuron or a pan-neuronal promoter. Initiation control regions of promoters, which are useful to drive expression of nucleic acids in a specific animal cell, are numerous and familiar to those skilled in the art. Virtually any promoter capable of driving expression of the subject nucleic acids can be used. In some embodiments, the promoter used to drive expression of a subject protein can be the Thy1 promoter (See, e.g., Llewellyn, et al., 2010, Nat. Med., 16(10):1161-1166). In some embodiments, the promoter used to drive expression of a subject protein can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the a subject nucleic acid sequence in a target cell.

In some embodiments, a promoter may be an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

Also provided herein are recombinant expression vectors containing a light-activated polypeptide-encoding nucleic acid or any variant thereof as described herein. Vectors according to the present disclosure also include vectors containing a nucleotide sequence that encodes an RNA (e.g., an mRNA) that when transcribed from the vector will result in the accumulation of a subject protein in the on excitable cells, e.g., neurons, in the target tissue, including accumulation of light-responsive ion channels on the plasma membrane. Vectors which may be used include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, UK (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the system and method of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

In some embodiments, the subject light-responsive proteins can be combined with various promoters and/or fluorescent proteins (XFP) for targeting specific neuronal populations in mammalian brains. For example, the following adeno associated vectors (AAVs) and components thereof may be used without limitation: AAV-CamKII-X-XFP, AAV-hSyn-X-XFP, AAV-mThy1-X-XFP, AAVmThy1-X-XFP, AAV-GFAP-X-XFP, AAV-VGAT-X-XFP, AAV-PET1-X-XFP, AAV-NPY-X-XFP, AAV-SST-X-XFP, AAV-AVP5.5-X-XFP, AAV-Ef1a-X-XFP, AAV-FLEX-rev-X-XFP, AAV-CAG-X-XFP, AAV-CAG-FLEX-X-XFP, where X is a light-responsive protein. Other AAV vectors that may be used in association with the polynucleotides include those with double floxed inverted reading frames (DIO) which allow expression of proteins under the control of recombinases such as Cre and Flp: AAV-Ef1a-DIO(Cre)-X-XFP (Cre-dependent expression), AAV-Ef1a-DIO(Flp)-X-XFP (Flp-dependent expression), AAV-Ef1a-DIO(Cre)-DIO(Flp)-X-XFP (Cre and Flp dependent expression), where X is a light-responsive protein.

Another major viral transduction system utilizes lentivirus including the following potential expression vectors: pLenti-CamKII-X-XFP, pLenti-Ef1a-X-XFP, pLenti-mThy1-X-XFP, pLenti-hThy1-X-XFP, pLenti-hSyn-X-XFP, pLenti-VGAT-X-XFP, pLenti-Hcrt-X-XFP, where X is a light-responsive protein. Herpes simplex virus (HSV) can be utilized to transport proteins of interest over synapses (anterograde) which includes the following expression vectors: HSV-EF1a-X-XFP and HSVEF1a-DIO-X-XFP, where X is a light-responsive protein. Rabies and pseudorabies virus can be utilized for retrograde transports over synapses using the following expression vector: SAD(delta)G-X-XFP and SAD(delta)G-DIO-X-XFP. Other mammalian expression vectors include: pcDNA3.1-CMV-X-XFP and pCAGGS-X-XFP, where X is a light-responsive protein.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); and an alpha subunit of Ca$(^{2+})$-calmodulin-dependent protein kinase II (CaMKIIα) promoter (see, e.g., Mayford et al. (1996) Proc. Natl. Acad. Sci. USA 93:13250).

In some embodiments, a non-human animal in which the target tissue is present is genetically engineered to express a light-responsive polypeptide, as described herein, by using any suitable method of genetically engineering the animal, e.g., via genetic manipulation of embryonic stem cells. In some cases, a cell in a target tissue is genetically modified to express a light-responsive polypeptide, as described herein. A genetically modified cell present in a target tissue can be present in a mammal, e.g., a human, a non-human primate, a rodent, a lagomorph, etc.

Any suitable method may be used to adapt excitable cells, e.g., neurons, to hyperpolarize and/or depolarize in response to a light stimulus. In some embodiments, excitable cells may be contacted with a viral vector containing a nucleic acid encoding a light-responsive polypeptide, by delivering the viral vector into the target tissue, locally or systemically. Where compositions are to be delivered to a site in the brain, stereotactic injection can be used; see, e.g., Stein et al., *J. Virol*, 73:34243429, 1999; Davidson et al., *PNAS*, 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties.

Utility

Embodiments of the present device and method find use in applications where it is desired to reduce/minimize artifacts in MRI, such as fMRI. As discussed herein, devices of the present disclosure include an optrode having a carbon fiber electrode. As compared to conventional metal wire electrodes, the carbon fiber electrode of the present device produces significantly less artifacts in MRI (e.g., fMRI). By significantly less artifacts is meant that the present device produces fewer artifacts in number and/or less severe artifacts in intensity as compared to conventional metal wire electrodes.

In some embodiments, the present device and method find use in screening in vitro and/or in vivo animal models of disease for neuronal circuit elements diagnostic of or causative for neuropsychiatric disease. In some embodiments, the present device and method find use in diagnosis of neuropsychiatric diseases of interest, which may include disorders of mood and affect, anxiety, psychosis, personality, etc. The animal model may be any suitable model, including, but not limited to, rodents, cats, dogs, monkeys, and non-human primates. Perturbations used to model a neuropsychiatric disease include genetic models of neurological or psychiatric disease, such as autism; chronically induced models as with kainate or pilocarpine-induced epilepsy or chronic stress-induced depression; and acutely induced models as with hallucinogens or psychotogenic agents such as ketamine or phencyclidine (PCP). By comparing the difference in activity pattern between neurons in normal target tissue and neurons in abnormal target tissue, neural correlates of the neuropsychiatric disorder may be identified. Optical control of neurons in the target tissue may then allow identification of causative neuronal activity patterns for a particular neuropsychiatric disorder. These manipulations may potentially provide novel treatment targets. As such, in some embodiments, the present device and method find use in diagnostic methods for neuropsychiatric diseases, e.g., where the diagnosis is carried out on a human or non-human mammalian subject.

In some embodiments, the present device and method find use in methods for identifying a treatment, e.g., a therapeutic treatment, with a desired activity on a group of neurons. If the desired outcome is known, then the present system and method may be used to screen for treatments, including, but not limited to, pharmacological agents, nonchemical based therapeutic treatment; behavioral treatment; electrical, magnetic, or optical based neural-modulation treatment; etc., that will bring about the desired neuronal activity pattern. The screening may be performed in any suitable animal model, either normal, or a model for a neurological disorder, such as Alzheimer's and Parkinson's disease, mild cognitive impairment, other dementias, and Down's Syndrome, as well as schizophrenia, autism, mood, affective, anxiety, and personality/developmental disorders.

In some embodiments, the present device and method find use in the treatment of a condition or disorder, such as a neurological or psychiatric condition using optogenetic control. As real time activity of neurons is monitored using the present device and method, a controller or processor may be configured to modulate the activity of neurons in response to the imaged activity signals in such a way as to treat or reduce symptoms of the condition or disorder, at the behavioral and/or physiological levels.

Computer Related Embodiments

A variety of computer-related embodiments are also provided. Specifically, the data analysis methods described herein may be performed using a computer, e.g., a processor. Accordingly, provided is a computer-based system for analyzing data produced using the above methods and devices in order to provide qualitative and/or quantitative analysis of a target area of interest in a subject.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include CD-ROM, DVD-ROM, BD-ROM, a hard disk drive, a ROM or integrated circuit, a magneto-optical disk, a solid-state memory device, a computer readable flash memory, and the like, whether or not such devices are internal or external to the computer. A file containing information may be "stored" on computer readable medium, where "storing" means recording information such that it is accessible and retrievable at a later date by a computer. Examples of media include, but are not limited to, non-transitory media, e.g., physical media in which the programming is associated with, such as recorded onto, a physical structure. Non-transitory media for storing computer programming does not include electronic signals in transit via a wireless protocol.

In certain embodiments, computer programming may include instructions for directing a computer to perform one or more assay steps as disclosed herein. For example, the computer programming may include instructions for directing a computer to detect and/or analyze signals acquired by the devices disclosed herein (e.g., the presently disclosed optrode). In certain embodiments, the computer programming includes instructions for directing a computer to analyze the acquired signals qualitatively and/or quantitatively. Qualitative determination includes determinations in which a simple yes/no result is provided to a user with respect to the presence or absence of a detectable signal. Quantitative determination includes both semi-quantitative determinations in which a rough scale result, e.g., low, medium, high, is provided to a user regarding the detectable signal and fine scale results in which an exact measurement of the detectable signal is provided to a user (e.g., a quantitative measurement of local field potentials in a target area of interest).

In some embodiments, the computer programming includes instructions for directing a computer to perform a uniplex analysis of an analyte in a sample. By "uniplex analysis" is meant that detection and analysis is performed on a single target area in the subject. For example, a single tissue area in the subject containing excitable cells may be analyzed. In some embodiments, the computer programming includes instructions for directing a computer to perform a multiplex analysis of two or more target areas in a subject. By "multiplex analysis" is meant that the two or more distinct areas of interest in a subject are analyzed. For example, two or more distinct tissue areas in the subject each containing excitable cells may be analyzed. In certain embodiments, the computer programming includes instructions for directing a computer to perform several multiplex assays in parallel substantially simultaneously.

With respect to computer readable media, "permanent memory" refers to memory that is permanent. Permanent memory is not erased by termination of the electrical supply to a computer or processor. Computer hard-drive, CD-ROM, DVD-ROM, BD-ROM, and solid state memory are all examples of permanent memory. Random Access Memory (RAM) is an example of non-permanent memory. A file in permanent memory may be editable and re-writable. Similarly, a file in non-permanent memory may be editable and re-writable.

Kits

Also provided are kits for practicing one or more embodiments of the above-described methods. The subject kits may vary, and may include various devices and reagents. Devices include those mentioned herein with respect to implantable devices or components thereof (such as optrodes as described herein). The kit may include one implantable device, or in other cases may include two or more implantable devices. Each implantable device may be provided in separate containers, such that the devices may be used individually as desired. Alternatively, two or more devices may be provided in the same container such that the two or more devices may be used concurrently. In some cases, the kit includes a packaging that contains a device (e.g., one or more devices as discussed above). The packaging may be a sterile packaging configured to maintain the contents of the packaging in a sterile condition.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form would be a computer readable medium, e.g., CD, DVD, Bluray, computer readable memory device (e.g., a flash memory), etc., on which the information has been recorded. Yet another form is a website address which may be used via the Internet to access the information at a removed site. Any convenient form of instructions may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

In preclinical studies, implanted electrodes can cause severe degradation of MRI images and hence are seldom used for chronic studies employing functional magnetic resonance imaging (fMRI). Carbon fiber optrodes (optical fiber and electrode hybrid devices) were developed, which can be utilized in chronic longitudinal studies aiming to take advantage of emerging optogenetic technologies, and compared them with the more widely used tungsten optrodes. Optrodes of the present disclosure, which were constructed using small diameter (~130 µm) carbon fiber electrodes, caused significantly reduced artifacts on functional MRI images compared to those made with 50 µm diameter tungsten wire, and at the same time the carbon electrodes had lower impedance, which led to higher quality intracranial local field potential (LFP) recordings.

In order to validate this approach, these devices were used to study optogenetically-induced seizure-like afterdischarges in rats sedated with dexmedetomidine and compared to sub (seizure) threshold stimulations in the same animals. The results indicated that seizure-like afterdischarges involved several extrahippocampal brain regions that were not recruited by subthreshold optogenetic stimulation of the hippocampus at 20 Hz. Subthreshold stimulation led to activation of the entire ipsilateral hippocampus, whereas afterdischarges additionally produced activations in the contralateral hippocampal formation, septum, neocortex, cerebellum, nucleus accumbens, and thalamus. Carbon fiber optrodes of the present disclosure can be utilised in a variety of studies that could benefit from longitudinal optogenetic functional magnetic resonance imaging (ofMRI).

Different optical fiber and electrode hybrid devices (commonly known as optrodes) were produced and tested for performing both optical stimulation and LFP recording within the MRI environment. These devices can be used in both optogenetic functional magnetic resonance imaging (ofMRI) and in experimental studies employing optogenetics and long-term electrophysiological recordings where MRI compatibility is desired. Different optrode designs were compared and it was determined that those constructed using small-diameter (e.g., ~130 µm) carbon fiber electrodes were well suited for the task as they had low impedance and also caused minimal susceptibility artifacts in functional MRI images. In order to validate this approach, these devices were used in combination with simultaneous LFP-ofMRI to study optogenetically-induced seizure-like afterdischarges.

Materials and Methods

Different devices for optogenetic stimulation and electrical recording in the MRI environment were fabricated and compared. These optrodes were used to study optogenetically-induced seizure-like afterdischarges using fMRI. In this section, the design and fabrication of these optrodes is described, and subsequently the in vivo testing and optogenetics experiments are described.

2.1 Implantable Optical Fiber

Figure 1:
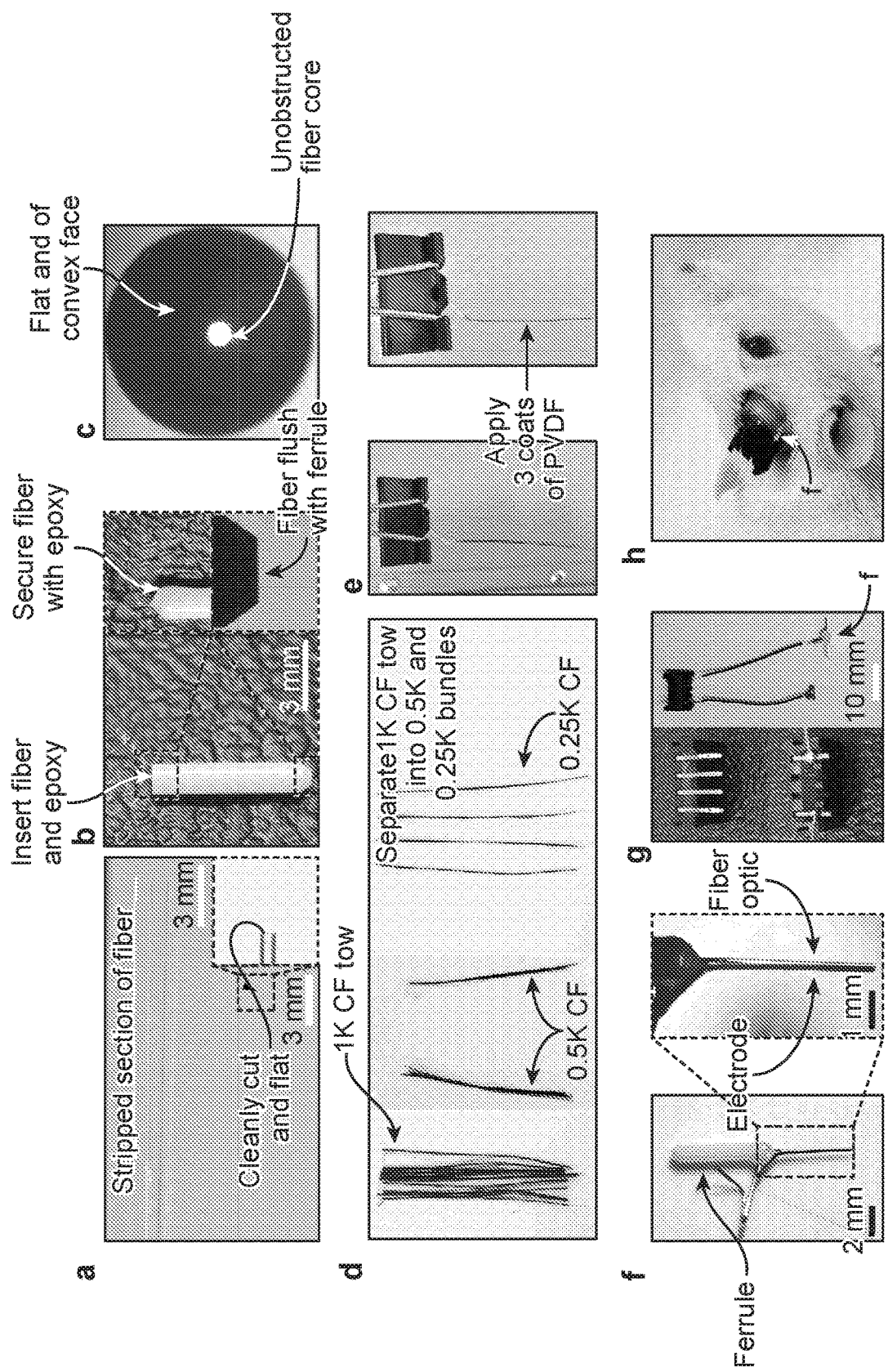
FIG. 1: Assembly of carbon fiber optrodes, according to embodiments of the present disclosure.

For optogenetic stimulation, light may be delivered through an optical fiber that is surgically implanted into the desired brain region (Sparta et al., 2012). Optical fibers for implantation were constructed using a 105 µm core diameter multimode optical fiber (FG105LCA, Thor Labs) inserted and secured into 1.25 mm diameter ceramic stick ferrules (Thor Labs, Newton, N.J.). The ferrules had a convex end, which connected to the light source, and a concave end, which was ultimately directed towards the brain. First, the optical fibers were stripped of their plastic coating and cleaved to the desired length (11 mm) using a high-precision fiber cleaver (Fujikura, CT-05, Tokyo, Japan) in order to maximize the reproducibility of light delivery to the brain. The cleaved optical fiber was examined to ensure that the ends were flat and cleanly cut (FIG. 1, panel a). Next, the section of fiber was then inserted into the ferrule through its concave end until the fiber was level with the convex face of the ferrule. Epoxy adhesive was applied on the concave side of the ferrule to secure the optical fiber in place (FIG. 1, panel b). The completed optical fiber implant was inspected using a light microscope to ensure that the fiber was not damaged and was free of debris. Examining the fiber along the optical axis, it was ensured that the fiber core remained intact and that light could pass unobstructed through the optical fiber (FIG. 1, panel c). Finally, light transmission was tested using an optical power meter (Newport Corp, CA) to ensure that it was greater than 80%.

2.2 Carbon Fiber Optrode Design and Fabrication

Optrodes used in optogenetics studies are typically comprised of materials that can create artifacts during MR imaging. The carbon fiber design discussed herein is an attempt to reduce these artifacts by replacing components that have large magnetic susceptibilities. Typical carbon electrode designs employed a brass screw as an electrical contact to the carbon fiber bundle. This metallic screw can cause artifacts in spiral readout fMRI images, which distorts the image in the cortex above the electrode. In the embodiments of the present disclosure, the metallic screw was replaced by a single wire to alleviate this problem. Typical carbon electrode designs also use a silver print to affix the carbon fiber bundle, which is too fragile and difficult to handle. To improve the strength and ease of fabrication of the electrodes of the present disclosure, silver epoxy was used as a conducting adhesive. Typical electrodes have a large diameter (400 µm diameter electrodes), which cause too much brain injury and are not suitable for chronic studies. Embodiments of the present disclosure use a range of smaller electrode diameters.

Individual carbon fiber electrodes were constructed out of 20-30 mm sections of 1K carbon tow (CST Composites, Tehachapi, Calif., USA). 1K tow includes approximately 1000 carbon filaments per tow (bundle). In order to produce different electrodes with different diameters, the 1K tow was split in half once to produce 0.5K bundles and twice to produce 0.25K bundles of carbon fiber. (FIG. 1, panel d). Individual carbon fiber bundles were cold soldered to a 10 mm section of stripped 30 AWG wrapping wire using conductive silver epoxy (MG Chemicals, Ontario, Canada). The epoxy was allowed to cure for at least 24 hours and following this the carbon fiber bundles were coated in a solution of the thermoplastic PVDF diluted with methyl isobutyl ketone at a 2:1 ratio. The bundles were dipped into PVDF, baked at 200° C. for 20 minutes and cooled at room temperature for 20 minutes. This process was repeated 3 times to ensure ample coating and insulation of the carbon fiber bundle (FIG. 1, panel e).

Carbon fiber electrodes were cut using surgical scissors to expose the contact point and were then fastened to the implantable fiber optic ferrules using epoxy adhesive, ensuring that they remained parallel and that the ends of the fiber optic and carbon fiber electrode met at the same point (FIG. 1, panel f). This ensured that the LFP recording took place at the site of optical stimulation. The wire attached to the carbon fiber electrodes was then soldered to a 3-4 cm section of wire attached to a press fit connector (part number: H3909-ND, Digi-Key, MN). A brass screw was soldered to the connector via a 30 AWG wire to serve as a cerebellar reference electrode (FIG. 1, panel g). Finally, the optrode was implanted into male adult rats for in vivo testing, as described below (FIG. 1, panel h).

2.3 Tungsten Optrode Fabrication

Tungsten optrodes were constructed using a method similar to that described by Armstrong et al. (Armstrong et al., 2013). Briefly, 50 μm perfluoroalkoxy alkane (PFA) insulated tungsten wire (A-M systems, WA) was attached to the implantable fiber optic (described above) using fine thread and epoxy adhesive. The tungsten microwire was cut so that the end of the electrode was in line with the end of the fiber. The other end of the microwire was soldered to the same connector used for the carbon fiber optrodes (FIG. 1, panel g) and similarly a brass screw was used as a reference electrode.

2.4 Impedance Measurements

The contact impedance of the electrodes was tested in 0.9% NaCl in distilled water. Briefly, a function generator (33210a, Agilent Technologies, Palo Alto, Calif.) was used to produce a constant voltage (1V peak-to-peak amplitude, 100 Hz) sine wave. The output terminal of the function generator was connected to a true root mean squared (RMS) digital multimeter (Fluke 87V, Fluke Corporation, WA) to measure the current flowing through the circuit. The other terminal of the ammeter was connected to a AgCl reference electrode (immersed in saline solution). The (carbon fiber or tungsten) working electrode was immersed in the saline solution to complete the circuit. The contact impedance magnitude of the electrode was calculated as the ratio of the RMS voltage across the test electrode (measured using an oscilloscope) and the RMS current flowing through the circuit.

2.5 MRI Phantom Construction, Imaging and Analysis

To compare the imaging artifacts induced by each electrode, a phantom was constructed in which tungsten (50 μm) and carbon fiber electrodes (approximate number of fibers: 1 K, 0.5K and 0.25K) were embedded in 2% agarose (G-Biosciences, St. Louis, Mo.) within a 50 ml Falcon tube. All magnetic resonance imaging was carried out at Stanford University using a 7T MR901 horizontal bore scanner (Agilent Technologies, Palo Alto, Calif.) and a shielded gradient system (600 mT/m, 6000 T/m/s). A two-channel 30 mm diameter Millipede transmit/receive volume coil (Agilent Technologies) was used for data acquisition. The phantom was oriented such that that the electrodes lay perpendicular to the main field. A fast spin echo (FSE) sequence was used to assess the artifacts caused by each electrode. The sequence parameters were as follows: TR=5 s, Echo train length (ETL)=8, effective TE (TEeff)=42 ms, matrix=384×384, field-of-view (FOV)=35×35 mm, slice thickness=0.5 mm, number of slices=23, number of averages=2. The acquired data was first smoothed using a Gaussian kernel with a full-width at half-maximum of 200 μm to reduce the effects of high-frequency noise. Following this, 1-dimensional signal intensity profiles were generated by taking the row of voxels at the center of the hypointense region and averaging across 7 consecutive slices, as these slices each contained all 4 of the electrodes. The center voxel for each electrode was taken to be the voxel located within the hypointense region that had the lowest signal intensity.

2.6 Virus Injection and Optrode Implantation

Adult male Sprague-Dawley rats (n=15 in total; 300-620 g; Charles River Laboratories, Wilmington, Mass.) were used for in vivo experiments. Animals were housed under a 12-hour light-dark cycle and provided with food and water ad libitum. Animal husbandry and experimental manipulation were in strict accordance with the National Institutes of Health (NIH) and Stanford University's Institutional Animal Care and Use Committee (IACUC) guidelines.

Optogenetics (Boyden et al., 2005; Zemelman et al., 2002) is a technique that utilizes opsins (light-sensitive proteins) to achieve millisecond-precise cell-type specific manipulation of neural activity in vivo. Channelrhodopsin2 (ChR2)-EYFP (enhanced yellow fluorescent protein) fusion protein viral expression system was used to express ChR2, a light-sensitive cation-selective channel (Nagel et al., 2003) under control of the Ca2+/calmodulin-dependent protein kinase IIα (CaMKII) promoter (expressed primarily in excitatory neurons). The viral plasmid was constructed by cloning CaMKIIα-ChR2(H134R)-EYFP into an adeno-associated virus (AAV) backbone using MluI and EcoRI restriction sites (map available online at www.optogenetics.org). The recombinant AAV vector was serotyped with AAV5 coat proteins and packaged by the University of North Carolina viral vector core (titer of ~4×1012 vg/ml). This viral construct was administered to the right-side of the hippocampus as described below.

During surgery, rats were anesthetized with isoflurane (induction 5%, maintenance 2-3%; Sigma-Aldrich, St. Louis, Mo., USA) and secured in a stereotactic frame. Following a midline incision, a small craniotomy and viral injection/optrode implantation were performed at the intermediate hippocampus (5.8 mm posterior to Bregma, 5.2 mm from the midline, and 3.1 mm from the dura). 2 μl of virus (n=11) or saline in controls (n=4) was delivered through a 34-gauge needle (World Precision Instruments Inc., FL) attached to a 10 μl Hamilton syringe at a rate of 150 nl/min. The syringe needle was left in place for 5 minutes before being slowly withdrawn.

The optrode was slowly inserted through an opening in the dura mater at the aforementioned coordinates, leaving 1-2 mm of uncoated fiber protruding from the brain. After cleaning the surface of the skull with hydrogen peroxide the optrode was secured to the skull using light-curable dental cement (Clearfil Liner Bond 2V, Kuraray America, Inc. NY). Just enough dental cement was added to cover the uncoated fiber as well as approximately half of the ferrule. As a result, the ferrule was held securely while at the same time there was enough space to connect the ferrule to the fiber optic patch cable. A brass screw was used as a support for the dental cement and also used as the reference electrode. This screw was fixed to the skull above the cerebellum at approximately 10 mm posterior to Bregma and 3 mm from the midline, and finally the connector, which was used to connect the electrodes to the lead wires, was mounted on the skull and secured with dental cement. Buprenorphine was injected subcutaneously pre- and post-operatively to minimize discomfort induced by the surgical procedure. In order to allow time for viral-mediated ChR2 expression, all optogenetics experiments were performed at least 6 weeks following virus injections.

2.7 In Vivo Assessment of MRI Artifacts and Data Analysis

In order to investigate the artifacts caused by 3 of the electrode designs (tungsten (n=5), 1K CF (n=4) and 0.25K CF (n=4)), implanted rats were anesthetized with 4% isoflurane and maintained at 2% throughout the duration of the experiment. Structural imaging was carried out using a FSE sequence with the following parameters: TR=5 s, TEeff=42 ms, ETL=8, FOV=30×30 mm, slice thickness=0.75 mm, number of slices=30, matrix=256×256, in-plane resolution=117×117 µm$^2$. Spoiled gradient echo (SPGR) with rectilinear sampling was also used to compare tungsten to 0.25K CF electrodes using the following sequence parameters: TR=0.6 s, TE=10 ms, FOV=30×30 mm$^2$, matrix=128×128, in-plane resolution=234×234 µm$^2$. Assessment of artifacts on fMRI scans was carried out using the functional imaging sequence described below. Following data acquisition, all of the reconstructed images were smoothed for noise reduction with a low bandwidth Gaussian kernel of 0.2 mm at FWHM to ensure the artifacts were not oversmoothed. In order to assess the artifact over a number of subjects, 1D signal intensity profiles were generated from one fMRI image frame in each subject. This was achieved by selecting the row of voxels in the middle of the hypointense region and normalizing this row of voxels to the average local signal intensity, where the local signal intensity was taken to be those voxels located between 4-8 voxels from the center voxel.

2.8 Optogenetic fMRI Experiments

Out of 13 rats used in the previous experiment, in 3 rats with 1K carbon fiber electrodes implanted, the ferrule holding the fiber optic was not held tightly enough by the dental cement and consequently became loose upon connecting the fiber optic patch cable. These rats were therefore excluded from this part of the study along with 2 rats implanted with tungsten optrodes and 4 control rats without virus injection. 4 of the rats previously injected with virus and implanted with carbon fiber (CF) optrodes, which were used for the experiments assessing MRI artifacts, were used for the ofMRI experiments. An additional 2 rats were also implanted with 0.25K CF electrodes for this part of the study (in total: 0.25K, n=5 and 1K, n=1). Seizure-like activity can be elicited in rats anesthetized using a mixture of nitrous oxide and isoflurane (Weitz et al., 2014). However, isoflurane can have significant anti-convulsant properties (Kofke et al., 1989). Therefore, in this experiment, the rats were sedated using a different anesthetic, dexmedetomidine hydrochloride, as it is known that rats have a higher propensity for seizures under dexmedetomidine sedation (Airaksinen et al., 2010; Choy et al., 2010; Fukuda et al., 2013; Mirski et al., 1994). Briefly, this regimen entailed initially anaesthetizing the animal using 4% isoflurane, followed by a 0.05 mg/kg bolus subcutaneous (s.c.) injection of dexmedetomidine (Dexdomitor, Pfizer, NY), followed by a continuous intravenous (i.v.) infusion of dexmedetomidine at a rate of 0.1 mg/kg/h via a 24 G catheter inserted into the lateral tail vein. After the initial induction, isoflurane concentration was gradually reduced to zero over a 10 min period. Rats were allowed to breathe room air spontaneously throughout the imaging sessions.

A custom-designed transmit/receive single-loop surface coil (inner diameter=22 mm, outer diameter=40 mm) was used for data acquisition. The coil was placed around the connector and ferrule, as close as possible to the rat's head. Functional imaging was implemented using a multi-slice Gradient Recalled Echo (GRE) sequence with a four-interleave spiral readout (Glover and Lai, 1998) using the following parameters: TR=750 ms, TE=12 ms, FOV=30×30 mm, number of slices=23, slice thickness=0.75 mm, inplane resolution=0.43×0.43 mm, number of frames=130. Images were reconstructed using 2-dimensional gridding (Fang and Lee, 2013; Jackson et al., 1991) and a sliding window reconstruction (Nayak et al., 2004; Riederer et al., 1988). Following image reconstruction, image realignment was achieved using the method described in Fang and Lee, 2013.

2.9 ofMRI Stimulation Paradigms

In this study we employed a 473 nm diode-pumped solid-state laser (Laserglow technologies, Toronto, Canada) for optogenetic stimulation and two different stimulation paradigms. The first paradigm was a subthreshold paradigm designed not to induce seizure-like activity. For this, we used a 6-cycle block design with a period of 60 s (20 s on, 40 s rest) preceded by a 30 s baseline. The stimulation parameters included a 20 Hz pulse train with a 15 ms pulse duration. The light intensity per laser pulse entering the brain for each rat was set at a level, which was below the threshold for inducing afterdischarges (74-185 mW/mm2). Light intensity entering the brain was estimated by assuming 80% of the light exiting the fiber patch cable was transmitted to the brain. 80% was used as a conservative estimate because upon testing before implantation, all ferrules transmitted at least 80% of the input light from the fiber optic cable. A second paradigm was used to investigate seizure-like afterdischarges. For this, the afterdischarge threshold was found by increasing the light intensity in steps of 92 mW/mm$^2$, until an afterdischarge resulted from a 20 s stimulation. At the light-intensity required for inducing afterdischarges, the stimulation paradigm included a 30 s baseline followed by a single 20 s stimulation (20 Hz, 15 ms pulse width, light intensity=92-555 mW/mm$^2$ at the fiber tip). A single-stimulus response measurement enabled monitoring of seizure progression at different stages throughout afterdischarges and also minimized the interaction between consecutive responses.

In order to control for potential heating-related artifacts (Christie et al., 2013; Desai et al., 2011), 3 of the 4 control animals, which were used earlier for assessment of MRI artifacts and which had been injected with sterile saline in place of AAV5, were imaged using the block design described above. One of the rats was not imaged because there was no evidence of any significant heating-induced signal changes in the first 3 rats that were imaged. A range of light intensities was tested, which included: 1293, 1663, 2310, 2587 mW/mm$^2$ per laser pulse at the fiber tip. At the 30% duty cycle used here, this was equivalent to time-averaged power densities at the fiber tip of 388, 499, 693 and 776 mW/mm$^2$ respectively. In 2 of the 3 animals, a single experiment using a 99% duty cycle and a time-averaged power density of 2561 mW/mm$^2$ at 10 Hz was carried out to determine the effect of very high light intensity on the fMRI response.

2.10 ofMRI Data Analysis fMRI data analysis was performed using SPM 12 (The Wellcome Trust Centre for Neuroimaging at University College London; Statistical Parametric Mapping) using a general linear model (GLM) in MATLAB 2014a (Mathworks, MA). Images were initially smoothed using a Gaussian kernel with a FWHM of 0.4 mm to improve the signal-to-noise ratio (SNR). For the block-design paradigm, the design matrix was created by convolving the stimulation period with the canonical haemodynamic response function (HRF). For the single-stimulation paradigm, two different analysis methods were used. First, to study activation dynamics, a time-resolved GLM analysis was used for the single-subject data. A sequence of three boxcar functions were used. These included the 20 s during the stimulation, 20 s post-stimulation and the rest of the afterdischarge as defined on the LFP recording. These were convolved with the canonical HRF to take into account the haemodynamic delay and used as a design matrix for the GLM. Activation maps were generated by comparing these active periods vs. baseline. Our goal was to compare the activation map during the 20 s suprathreshold stimulation against the activation map generated during the first 20 s of the afterdischarge. Second, for the group analysis, because the number of subjects was low, a multi-subject 1st level design (fixed-effects model) was used. In this analysis, the afterdischarge itself was of interest and therefore regressors included the stimulation period and the entire period during the afterdischarge as defined on the simultaneously recorded LFP. At the subject level, in order to correct for multiple comparisons, voxels were deemed to have a significant response if their voxel-wise false discovery rate (FDR) corrected p-value was less than 0.01. At the group-level analysis, a stricter threshold of $p<0.001$ (FDR corrected) was used.

2.11 LFP Recordings and Analysis

Monopolar single channel intracranial LFP was recorded at a sampling rate of 5 kHz from the hippocampal depth electrodes using the Biopac MP150 data acquisition system and EEG100C-MRI amplifier (Biopac Systems, CA). The cerebellar screw electrode was used as the reference electrode. For recordings taking place in the MRI scanner, a ground electrode was not needed due to the electrically quiet environment. For the awake recordings, a subcutaneous electrode was placed under the skin and used as a ground electrode. LFP quality was tested by using awake recordings in 6 rats (n=3 0.25K CF and n=3 tungsten). Average power across the 4 different frequency bands was calculated by using the bandpower function in MATLAB from 60 s of recording. Subthreshold and suprathreshold stimulations were carried out in 2 awake rats using the same paradigm as the fMRI experiment. To calculate the LFP spectral power over time, band power was calculated over 3 s windows corresponding to 4 TRs and this was normalized to the baseline period. The 0.1 Hz high-pass, 35 Hz low-pass filters on the amplifier were used in conjunction with the Biopac radiofrequency filtered cable system. In order to minimize gradient-induced artifacts, the electrode leads were used in a twisted pair configuration. Using this setup, in combination with the low-pass filter and the signal processors on the EEG100C-MRI amplifier reduced the gradient artifact to amplitudes comparable to or below the amplitude of the LFP signal. Where necessary, artifacts were further reduced using the FMRIB plug-in for EEGLAB (Allen et al., 2000; Niazy et al., 2005) using timing triggers from the radiofrequency amplifiers. In general, the use of a hardware filter at such a low cutoff frequency can remove valuable information from the gamma frequency range and therefore may not be desirable depending on the study requirements.

2.12 Histology

In order to confirm ChR2 expression in the targeted region, 2 rats were perfused with 0.1M phosphate-buffered saline (PBS) and ice-cold 4% paraformaldehyde in PBS. 50 μm coronal sections were prepared on a freezing microtome (HM 430, ThermoScientific) and imaged using a widefield fluorescence microscope (Leica EL6000).

Results 3.1 Impedance Testing

The aim of this study was to investigate different strategies for MRI compatible, chronic extracellular field recordings for ofMRI. First, in order to determine their suitability for field recordings, the contact impedance magnitude of the 4 different electrodes was tested on the bench by immersing the electrodes in an electrolyte consisting of 0.9% saline and passing a 100 Hz alternating current through a circuit formed with a reference electrode. The results from this experiment (displayed in Table 1) indicated that the 50 μm diameter tungsten wire electrodes had the highest impedance (591±110 kΩ) and as was expected, the impedance of the carbon fiber electrodes increased with decreasing diameter. Even the smallest diameter (128 μm) 0.25K carbon fiber electrodes tested here had a lower impedance (79±4 kΩ) than the 50 μm diameter tungsten wire electrodes commonly used for LFP recordings, indicating that these CF electrodes should lead to higher SNR LFP recordings.

3.2 MRI Imaging of Electrodes Embedded in an Agarose Phantom

Figure 2:
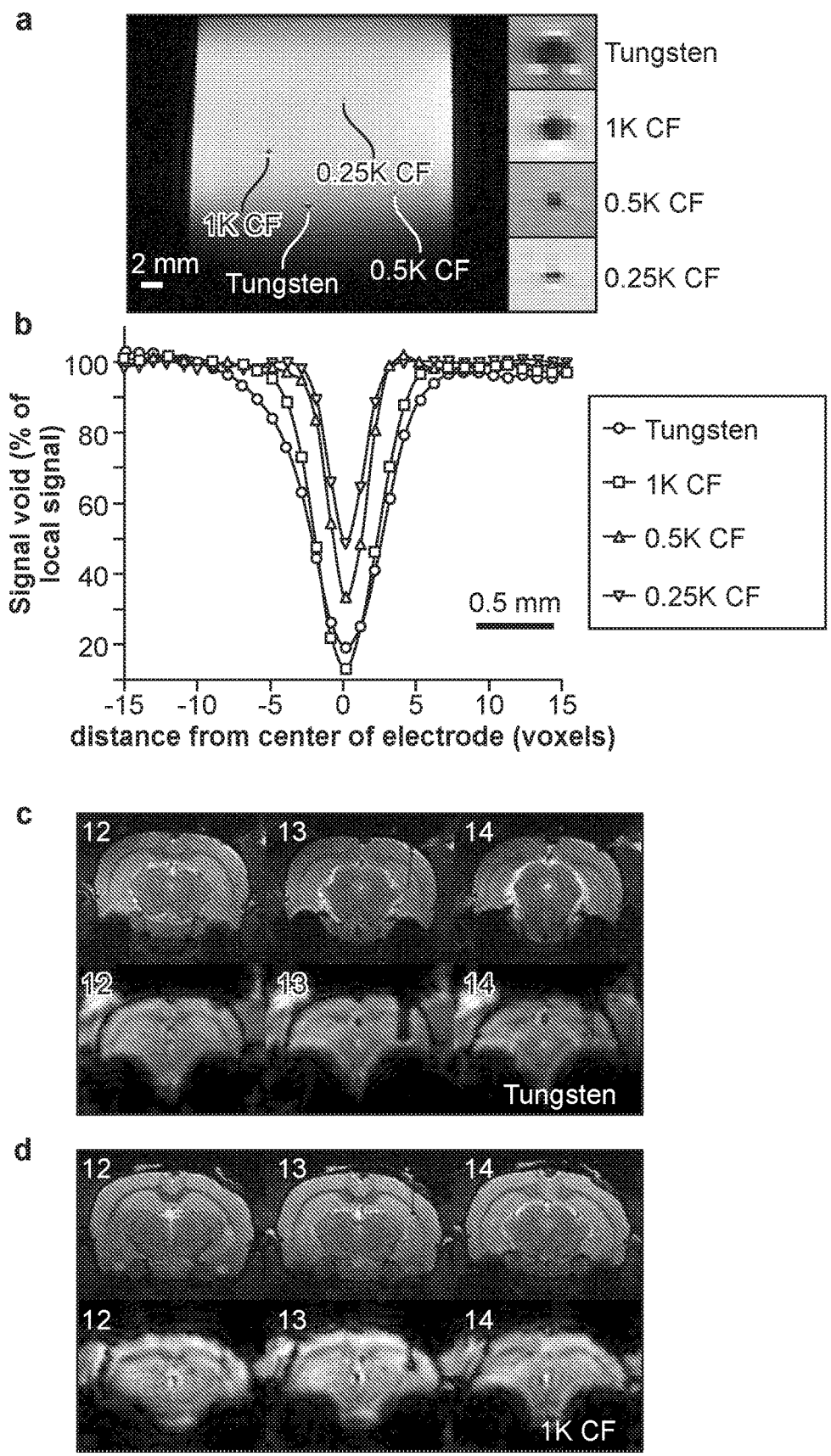
FIG. 2: Comparison of MRI artifacts and LFP quality for tungsten and carbon fiber optrodes, according to embodiments of the present disclosure.
Figure 2:
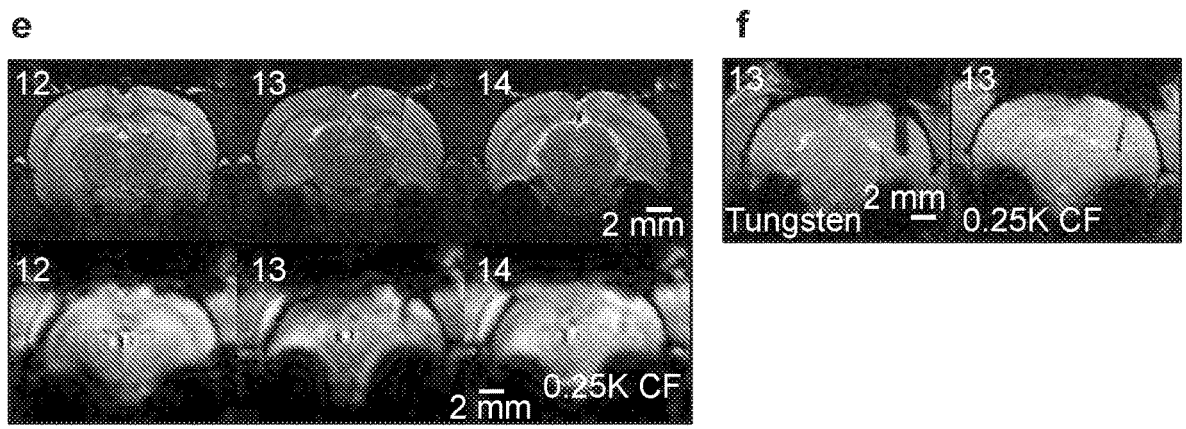
Figure 2:
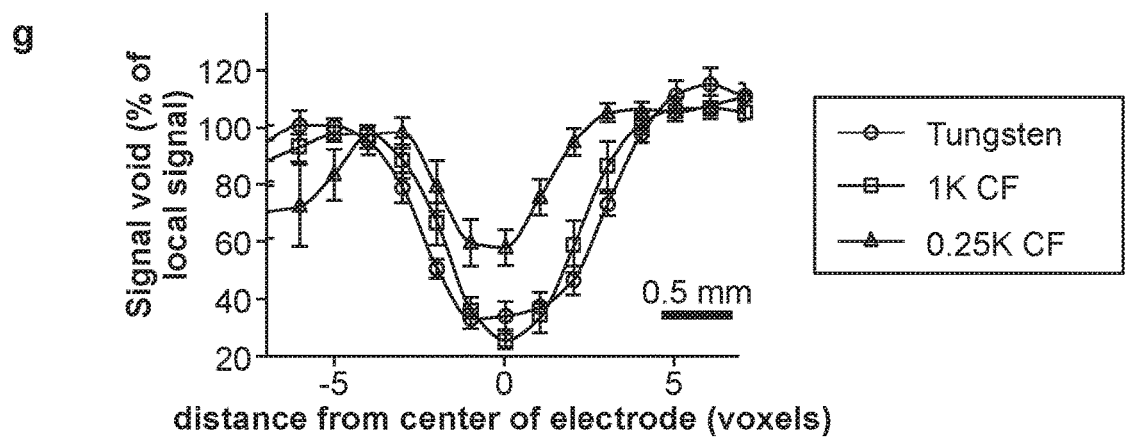
Figure 2:
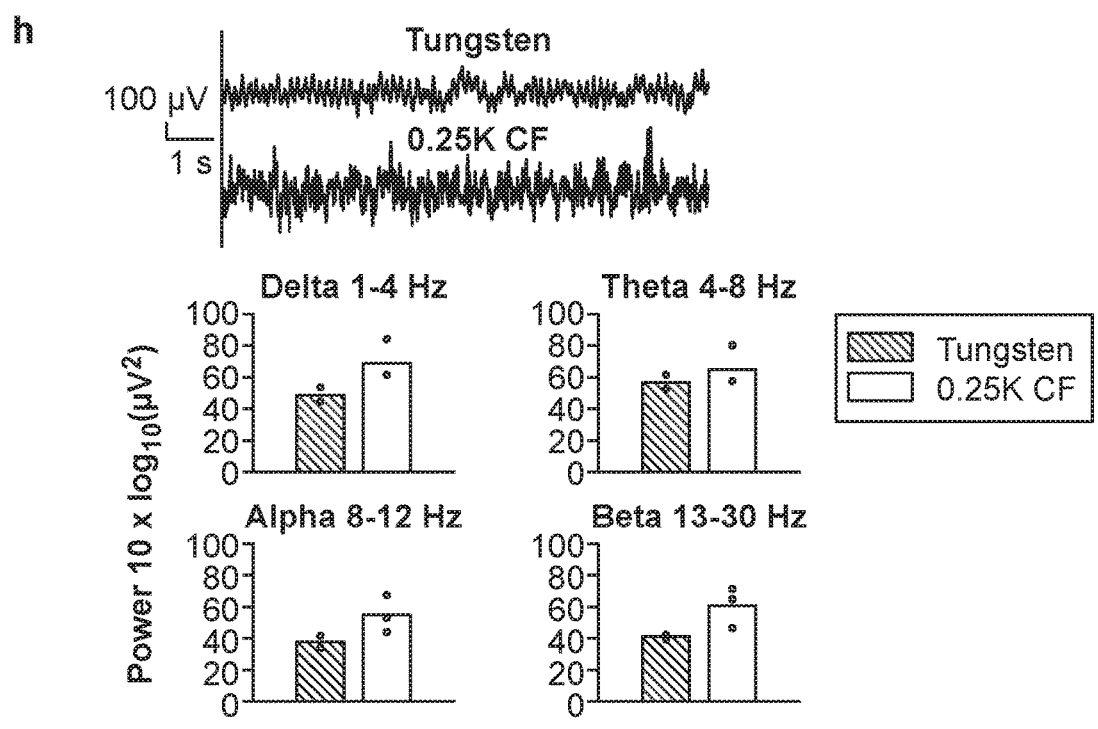

The FSE image of the MRI phantom is shown in FIG. 2, panel a. The size of the artifacts caused by the 1K CF electrode and the 50 μm diameter tungsten electrode were of a similar magnitude. The 0.5K and 0.25K CF electrodes caused significantly less artifact than the tungsten or 1K CF electrode. The 1-dimensional profiles, averaged across several slices are displayed in FIG. 2, panel b. From this figure it can be seen that the distortion caused by the tungsten and 1K CF electrodes was extensive and spread to approximately 5 voxels from the center of the electrode. The distortion caused by the 0.5K and 0.25K CF electrodes was much more modest and only spread to approximately 2 voxels from the center. In order to further investigate this, optrodes constructed using the tungsten, 1K CF and 0.25K CF electrodes were implanted into live animals for in vivo validation. As other studies (Dunn et al., 2009; Jupp et al., 2006) have used thicker diameter carbon electrodes (>0.4 mm), 1K CF and 0.25K CF optrodes were both tested in order to determine the most suitable diameter for in vivo studies.

3.3 In Vivo Assessment of Optrode Artifacts on MRI

In order to assess the imaging artifacts caused by each of the different optrode designs, structural (FSE) and functional spiral readout GRE imaging was carried out on a high-field 7T MRI scanner. In vivo images of the implanted optrodes are shown in FIG. 2, panels c, d, and e for the tungsten, 1K CF and 0.25K CF electrodes, respectively. Artifacts from the optrodes were much more evident on the GRE images compared to the FSE images for all 3 designs (FIG. 2, panels c, d, e, and f), which indicated the artifacts were primarily caused by magnetic field inhomogeneity. As was hypothesized from the phantom data, the tungsten optrodes caused the most significant degradation of GRE images, followed by the 1K CF and 0.25K CF electrodes. The 50-μm diameter tungsten electrodes eliminated signal from approximately half of the ipsilateral hippocampus from the imaging slice in which it was located (FIG. 2, panel c). Similar to the phantom data, quantification across animals was achieved by averaging the 1D profiles along the axis perpendicular to the electrode (FIG. 2, panel g). The plot of averaged 1D profiles showed that 0.25K CF implanted optrodes caused consistently less image distortion surrounding the electrode than either the optrodes constructed using the 1K CF or tungsten electrodes.

3.4 Awake LFP Recordings

Between 2-3 months following optrode implantation, awake intracranial LFP recordings were carried out in 6 rats implanted with either tungsten (n=3) or 0.25K CF electrodes (n=3). Examples of these awake LFP recordings are shown in FIG. 2, panel h. The average power within 4 frequency bands: delta, theta, alpha and beta was used as a measure of data quality. 1 rat in the tungsten group was excluded as no signal could be obtained. As to be expected from the impedance measurements in saline, the average power was higher across all frequency bands in the 0.25K CF group compared to the tungsten electrode group (FIG. 2, panel h). In one rat implanted with a 0.25K CF electrode, the total RMS noise was estimated to be 5 µV by recording shortly after death, indicating that these increases in LFP amplitudes are unlikely to be due to increased noise.

To investigate seizure-like afterdischarges using LFP and fMRI, two rats were tested awake and under dexmedetomidine to compare seizure thresholds in the awake vs. sedated state. Previous studies have suggested that dexmedetomidine lowers seizure thresholds (Mirski et al., 1994), however in both of the rats tested here, the light power density needed to elicit seizures was marginally higher (~92-185 mW/mm$^3$) in the sedated compared to the awake state, indicating that dexmedetomidine did not significantly potentiate seizures using our stimulation protocol.

3.5 Control of MRI Experiments

Typically, there is the potential for artifactual fMRI responses (Christie et al., 2013; Desai et al., 2011; Lee et al., 2010) when delivering light to the naïve (or opsin-negative) brain. These responses were characterized under the presently disclosed experimental setup to ensure that the results presented here were solely due to optogenetic manipulation. Upon preliminary investigation, heating artifacts at light intensities below 500 mW/mm$^2$ were not observed. Therefore, to determine the full relationship between light intensity and fMRI response a range of (time-averaged) light intensities between 388 and 2561 mW/mm$^2$ was investigated. Even time-averaged light power densities as high as 499 mW/mm$^2$ were unable to generate a measureable response and no voxels reached the significance level at the site of stimulation in any of the 3 rats tested (FDR corrected p<0.01) (FIG. 6, panels a and b). On the other hand, power densities of 693 mW/mm$^2$ or greater resulted in a small clusters of negative fMRI signal change directly below the fiber optic tip (FIG. 6, panels a and b). In 2 experiments (n=2), a very high time-averaged power density of 2561 mW/mm$^2$ was investigated. In one of these acquisitions, there was an extensive pattern of negative fMRI signal changes surrounded by positive fMRI signal changes (FIG. 6, panels a and b). In the other animal, this same laser power provoked only negative fMRI signal changes. The range of time-averaged light intensities required for the ofMRI experiments reported in this study was 56-167 mW/mm$^2$ which was far below the threshold required to generate artifactual fMRI signal changes (~693 mW/mm$^2$). Hence, the data from these control experiments rule out the possibility of artifactual responses in the ofMRI experiments.

3.6 ofMRI Investigation into Seizure-Like Afterdischarges

Figure 3:
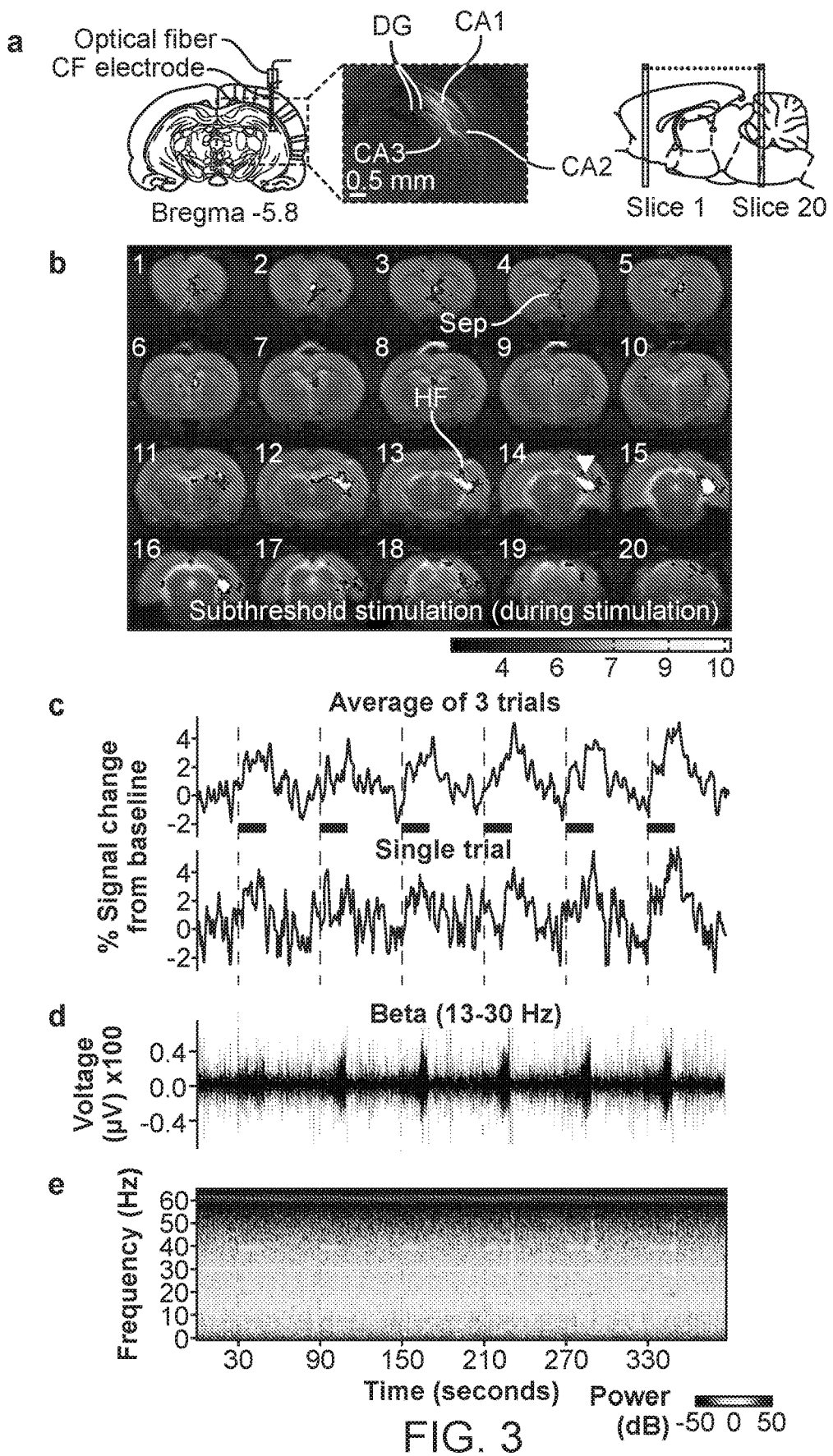
FIG. 3: Single subject simultaneous LFP and optogenetic fMRI during subthreshold stimulation of the hippocampus, according to embodiments of the present disclosure.
Figure 4:
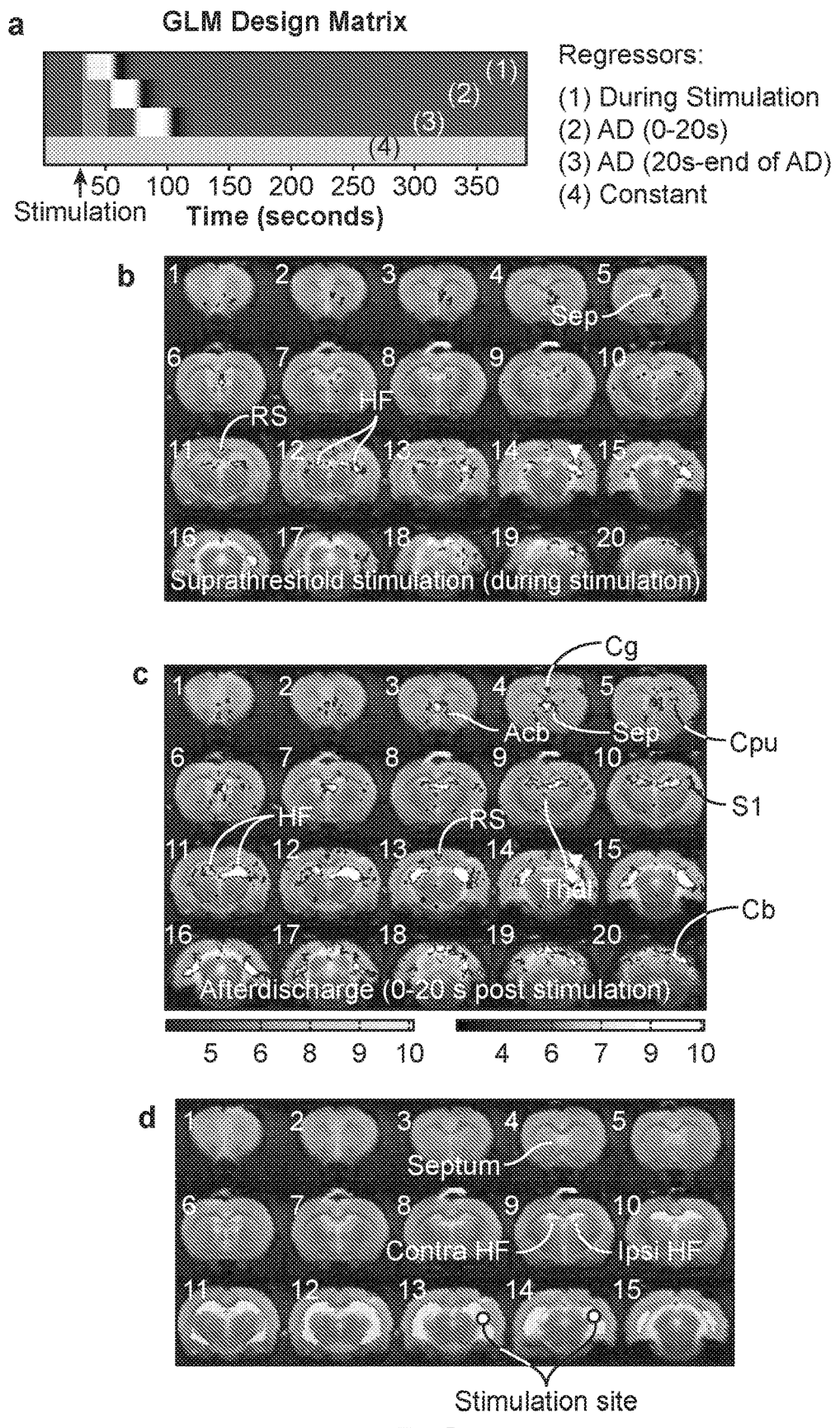
FIG. 4: Single subject simultaneous LFP and optogenetic fMRI during seizure-inducing (suprathreshold) stimulation of the hippocampus, according to embodiments of the present disclosure.
Figure 4:
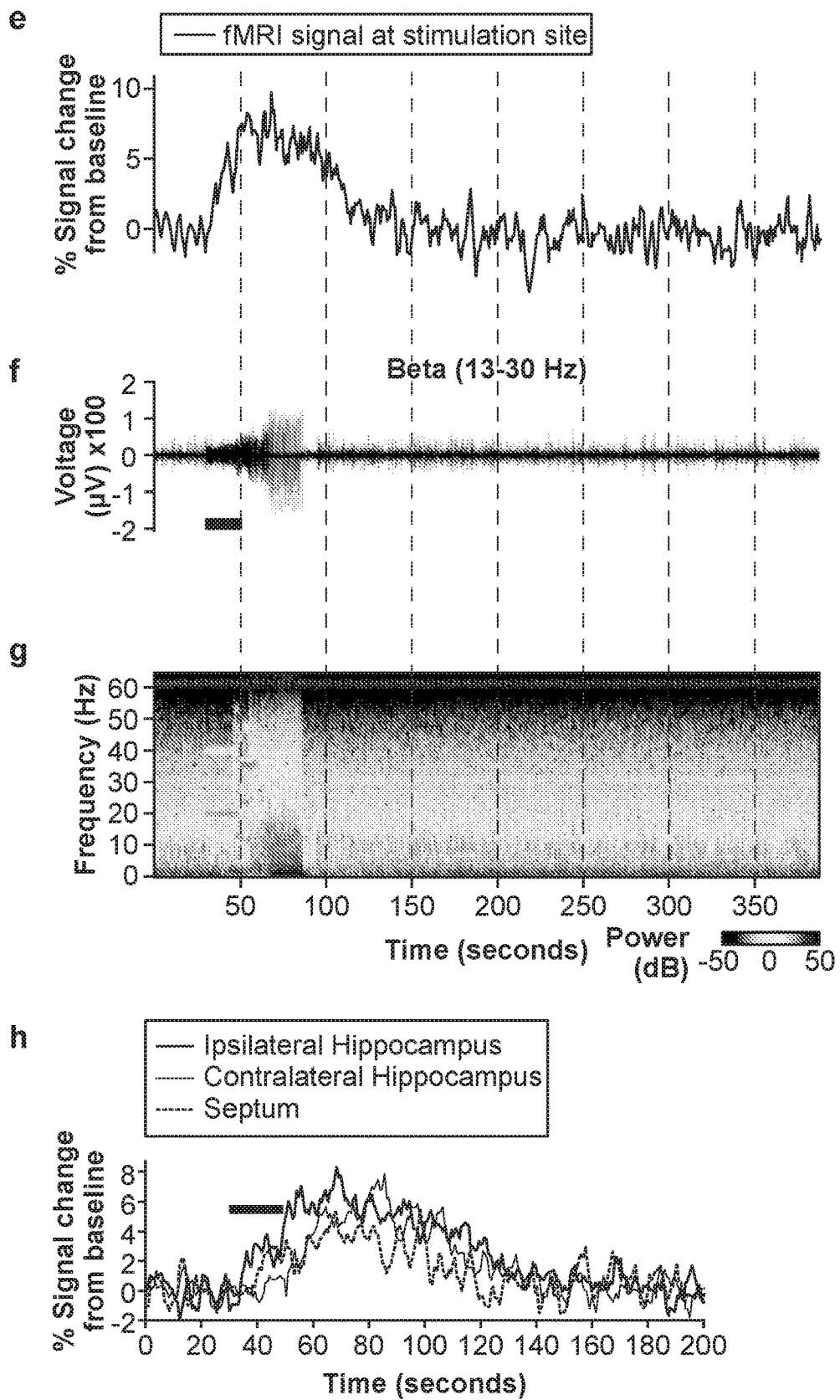

Initially, two rats were perfused in order to confirm histologically that the surgical procedure led to ChR2-EYFP expression in the right-side of the intermediate hippocampus (FIG. 3, panel a). Next, in order to validate the CF optrodes for use in chronic ofMRI studies, optogenetic fMRI experiments using 2 different stimulation paradigms were performed. Simultaneous LFP-fMRI was used to investigate the difference between subthreshold stimulations and stimulations using light intensities capable of eliciting seizure-like afterdischarges in rats sedated with dexmedetomidine. Stimulation of one of the rats did not result in afterdischarges even with high light intensity (1295 mW/mm$^2$) and this data was therefore excluded from the analysis. This could have occurred due to a possible mismatch between the virus injection and optrode locations. Subthreshold stimulation of the intermediate hippocampus resulted in activation confined primarily to the posterior ipsilateral hippocampal formation (HF)—primarily the dentate gyrus and CA3 subregions—as well as to the septum (Sep), most significantly within the lateral septum ipsilateral to the site of stimulation (FIG. 3, panel b). Simultaneous LFP recording using the CF electrodes at the site of stimulation confirmed an increase in amplitude in the Beta band (13-30 Hz) during the stimulation and confirmed an absence of seizure-like afterdischarges (FIG. 3, panels d and e). During a suprathreshold simulation, in addition to the ipsilateral hippocampus and septum, positive BOLD signal changes presented throughout the ipsilateral and contralateral hippocampus (septal and temporal regions), and the retrosplenial (RS) cortex (FIG. 4, panel b). During the optogenetically-induced afterdischarge, significant activation was much more widespread throughout the HF and septum in both hemispheres and also throughout the cortex and in addition included the cingulate (Cg) primary somatosensory (S1) and cerebellum (Cb) (FIG. 4, panel c). Within the basal ganglia, significant activation was present in the accumbens nucleus (Acb) and there were limited regions of negative signal change within the caudate putamen (CPu). Finally, the subject-level activation map showed that there was limited activation in the midline nuclei of the thalamus (Thal). To investigate the time course of activation, 4 of the most significantly activated regions were segmented on the structural images: ipsilateral hippocampus, contralateral hippocampus and septum, and the site of stimulation (FIG. 4, panel d) and the ROI at the site of stimulation shows a large BOLD response during the stimulation and throughout the afterdischarge (FIG. 4, panel e) whilst the presence of epileptiform afterdischarges was confirmed using simultaneous LFP recording at the stimulation site (FIG. 4, panels f and g). These manifested as mid-low frequency<20 Hz, high amplitude fluctuations lasting 79±12 s (13 afterdischarges in 5 rats). The time course of BOLD signal change throughout the stimulation and afterdischarge shows time delays between the fMRI responses in different brain regions during an epileptic discharge, e.g., activity in the contralateral hippocampus followed the septum, which in turn followed the ipsilateral HF (FIG. 4, panel h).

Figure 5:
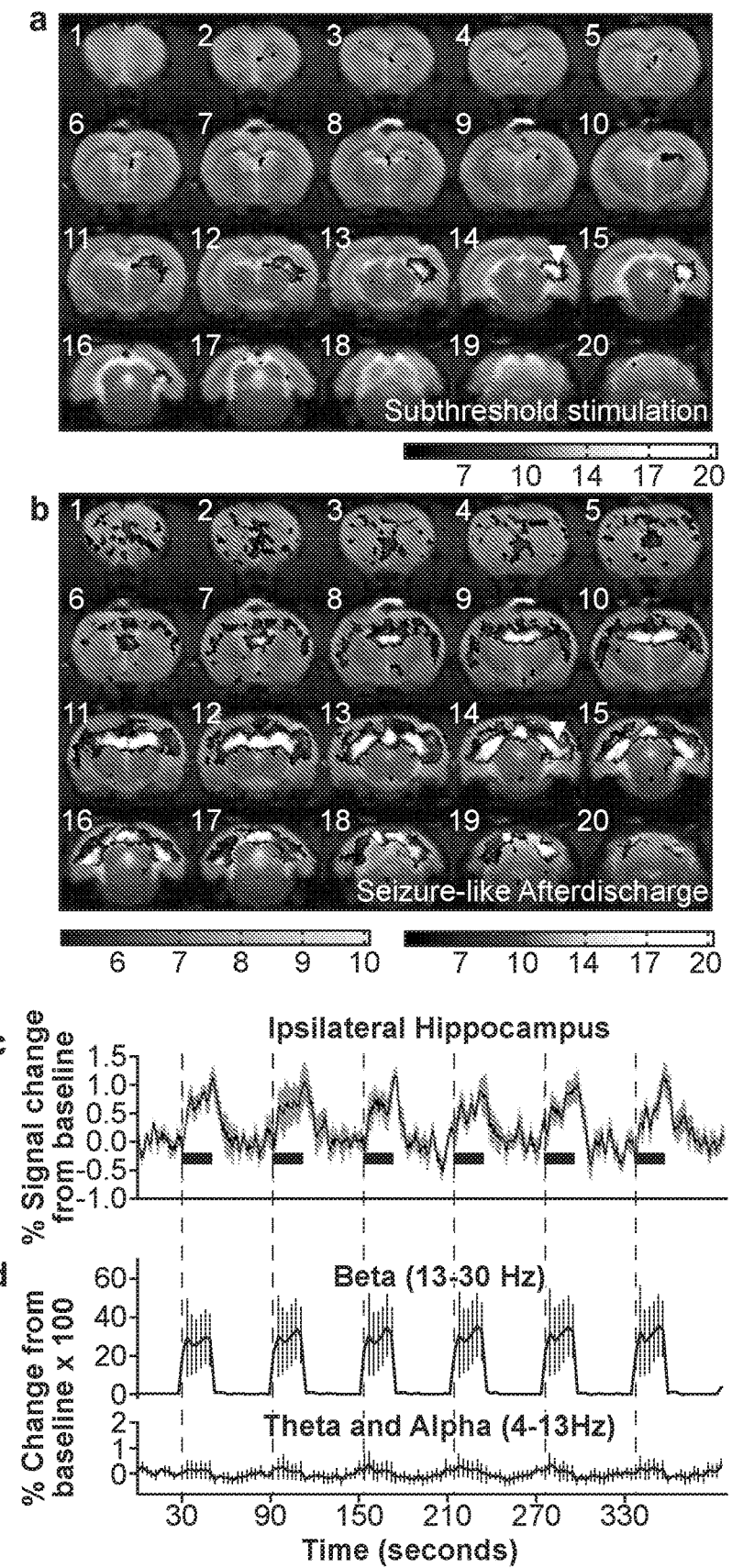
FIG. 5: Group-level analysis of fMRI data, according to embodiments of the present disclosure.
Figure 5:
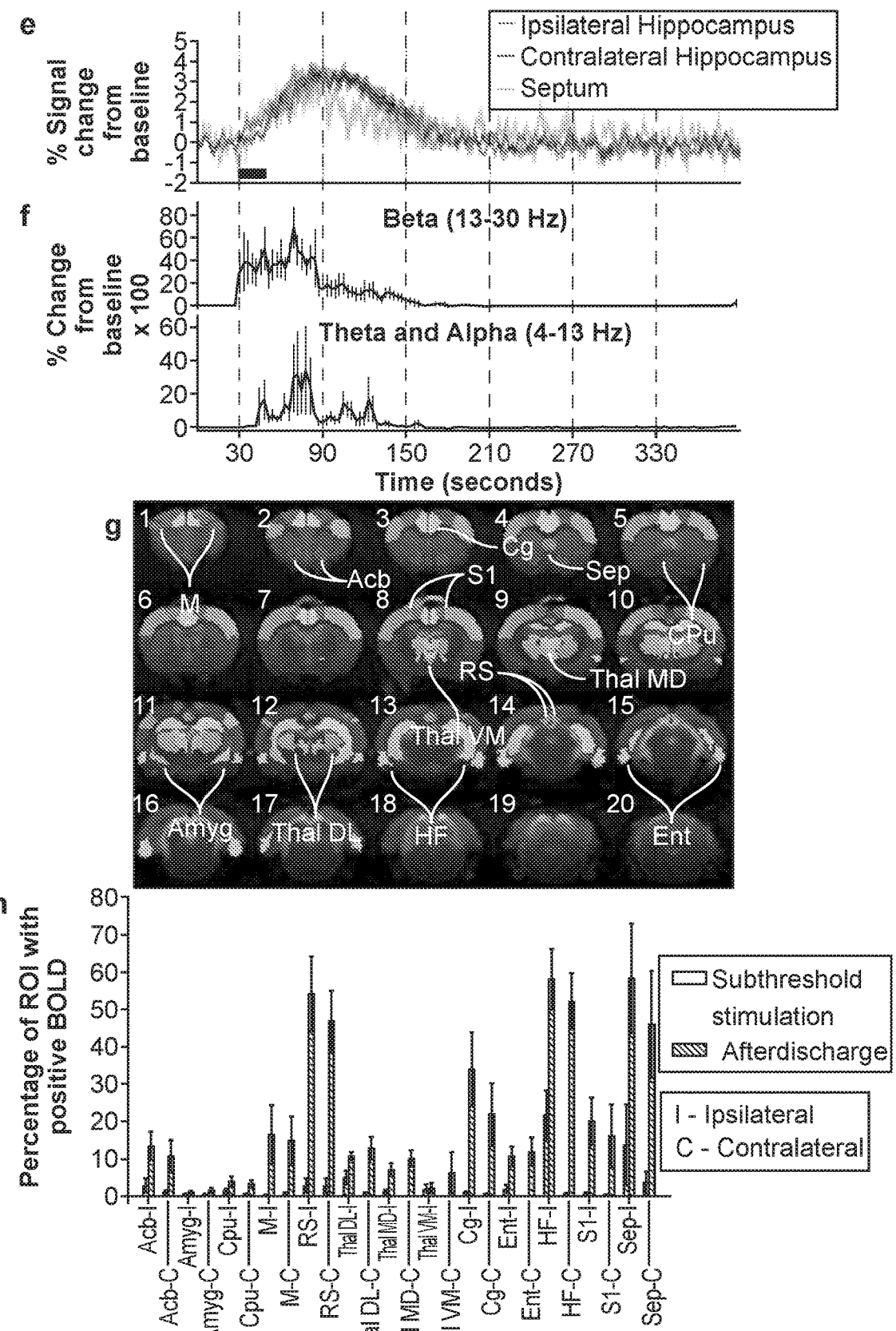

In order to quantify these effects at the group level, the subjects were coregistered together in order to generate group-level activation maps. These group-level activation maps (FIG. 5, panels a and b) also indicated that during subthreshold stimulations, activity was localized to the ipsilateral HF and septum. On the other hand, during afterdischarges, activation was located throughout the entire HF, septum, retrosplenial, cingulate and cerebellar cortices, as well as limited regions within the somatosensory and motor cortices. The fMRI time courses averaged across subjects for the subthreshold and suprathreshold stimulations are shown in FIG. 5, panel c and e, respectively. For the afterdischarge stimulation paradigm, the response in the septum appeared to be slightly delayed relative to the ipsilateral hippocampus and similar to the single-subject data shown in FIG. 4, panel h. There may be a delay between the BOLD response in the septum and the response within the contralateral hippocampus. The averaged LFP band power showed increases in the Beta band during the subthreshold stimulation (FIG. 5, panel d), while the suprathreshold stimulation resulted in increases in Theta, Alpha and Beta during the afterdischarge period (FIG. 5, panel f). 13 different brain regions were segmented both contralaterally and ipsilaterally to the stimulation site (FIG. 5, panel g) and percentage of positive BOLD within a ROI was used to compare subthreshold stimulations to afterdischarges. The results from this analysis are shown in FIG. 5, panel h. For the subthreshold stimulation, in all 5 rats activity was localized to the ipsilateral HF and in 2 of 5 rats it was also present in the septum (FIG. 5, panels a and h). During the afterdischarge, activity was present throughout the contralateral HF in all rats (FIG. 5, panels b and h). On average 52% of the contralateral hippocampus ROI exhibited activation during the afterdischarge compared to 0.6% during the subthreshold stimulation. The retrosplenial cortex (RS) and the ipsilateral cingulate, somatosensory and motor cortices were activated in all subjects during the afterdischarge. Within the thalamus, primarily the dorsal-lateral (DL), and medial-dorsal (MD) subregions displayed the most significant activation.

FIG. 6 shows images of ofMRI at different time-averaged light power densities in control (saline injected) rats not expressing ChR2. FIG. 6, panel a, shows T-statistic maps showing regions of significant positive and negative fMRI signal changes at different light power densities (388-2561 mW/mm$^3$). For power levels 388-776 mW/mm$^3$, stimulation paradigms included 20 s trains of 20 Hz, 15 ms pulse duration (30% duty cycle), whereas for the 2561 mW/mm$^3$ level, a 99% duty cycle was used at 10 Hz. FIG. 6, panel b, shows a bar graph displaying mean percentage of ROI exhibiting significant negative fMRI signal change at different power levels (n=3 for 388-776 mW/mm$^3$ and n=2 for 2561 mW/mm$^3$). Quantification was performed using a circular ROI placed below the optrode and consisted of 7 voxels in diameter across 2 consecutive slices (right panel). Site of optical stimulation is marked by an inverted triangle. T-statistic maps were thresholded at a significance level of $p<0.01$, voxel-wise FDR corrected. These data indicated that the time-averaged light-intensity range used for ofMRI experiments (56-167 mW/mm$^2$) was far below the range that generates artifactual responses.

High-field MR compatible optrodes were produced according to embodiments of the present disclosure for simultaneous optogenetic stimulation and electrophysiological readout. The carbon fiber optrodes had significantly less MRI susceptibility artifacts than implanted tungsten electrodes. Furthermore, their suitability for high quality LFP recordings was demonstrated by their lower contact impedance than traditional tungsten electrodes. In order to validate these devices in vivo, optogenetic fMRI was used to compare seizure-like afterdischarges to subthreshold optogenetic stimulation of the hippocampus. The experiments presented herein demonstrate the feasibility of using MRI compatible carbon fiber optrodes for chronic optogenetic studies. Furthermore, these results indicated that the presently disclosed carbon fiber electrodes can be used for multi-site recordings with minimal brain injury and without significant degradation of fMRI image quality.

TABLE 1

| Electrode | Mean Diameter (μm) | Impedance magnitude (kΩ) |
| --- | --- | --- |
| Tungsten | 50 | 591 ± 98 |
| Carbon fiber 1K | 283 ± 11.6 | 28.9 ± 1.6 |
| Carbon fiber 0.5K | 171 ± 15.4 | 47.2 ± 5.6 |
| Carbon fiber 0.25K | 128 ± 9.9 | 79.1 ± 4.0 |

Table 1 shows impedance magnitude measurements at 100 Hz in saline for tungsten and carbon fiber electrodes constructed at different diameters. Diameters and impedances were reported as ±standard error of the mean. Tungsten electrodes (n=5), carbon fiber 1K (n=5), carbon fiber 0.5K (n=6), carbon fiber 0.25K (n=6).

FIG. 1 shows images of the assembly of carbon fiber optrodes. FIG. 1, panel a, shows an image of a 105 μm core diameter fiber optic that was stripped of its plastic coating, and cleaved to a predetermined length. The end of the fiber (black triangle) appeared to be flat and free of cracks when viewed under a light microscope. (FIG. 1, panel b) The fiber was then inserted into the concave end of a 1.25 mm ceramic ferrule and secured with epoxy adhesive. A correctly inserted fiber optic appeared flush with the convex end of the ferrule. FIG. 1, panel c, shows an image of the end of the ferrule, which can be checked under a light microscope to ensure that light passed unobstructed through the fiber optic. FIG. 1, panel d, shows an image of a 1K carbon fiber tow that was separated into two bundles, and each bundle was separated again to make four 0.25K bundles from one 1K bundle. FIG. 1, panel e, shows images of each 0.25K bundle that was then attached to a section of wire using silver conductive epoxy, and coated with three layers of a PVDF solution. Finished carbon fiber electrodes appeared straight and evenly coated. FIG. 1, panel f, shows an image of a carbon fiber electrode and implantable fiber optic that were secured together using epoxy adhesive. When viewing the optrode under a light microscope (right panel), the electrode and fiber optic ran parallel to each other. FIG. 1, panel g, shows an image of unused contacts that were removed from the press fit connector. To complete the assembly, the implant was soldered opposite a brass screw, which was used as a reference electrode. FIG. 1, panel h, shows an image of completed implants that were surgically implanted into Sprague-Dawley rats.

FIG. 2 shows images and graphs of a comparison of MRI artifacts and LFP quality for tungsten and carbon fiber optrodes. FIG. 2, panel a, shows an FSE MRI image of different electrodes embedded in an agarose phantom. FIG. 2, panel b, shows a graph of 1D profiles of the signal intensity through the center of each electrode in the phantom averaged across 7 slices showing signal void (as a percentage of local signal intensity) vs. distance from center of electrode. FIG. 2, panel c to FIG. 2, panel e, shows images of in vivo structural (FSE) and functional 4-interleave spiral readout GRE (average of 520 frames) MRI images showing rats implanted with optrodes constructed out of (FIG. 2, panel c) tungsten microwire, (FIG. 2, panel d) 1K CF and (FIG. 2, panel e) 0.25K CF electrodes. FIG. 2, panel f, shows an image of a standard SPGR with rectilinear sampling comparing tungsten and 0.25K CF electrodes. FIG. 2, panel g, shows a graph of mean 1D profiles for the spiral readout functional MRI images of the signal intensity through the center of each optrode for each of the different designs. Error bars represent the standard error of the mean. Tungsten (n=5), 1K CF (n=4), 0.25K CF (n=4). FIG. 2, panel h, shows graphs of example LFP recordings and average power within different LFP frequency bands for tungsten (n=2) and 0.25K CF electrodes (n=3) measured in awake rats 2-3 months after implantation.

FIG. 3 shows images and graphs of single subject simultaneous LFP and optogenetic fMRI during subthreshold stimulation of the hippocampus. FIG. 3, panel a, shows images of: Left panel—schematic indicating location of stimulation (blue triangle) and recording electrode line (black line); Middle panel—50 μm thick coronal section showing EYFP expression in the right hippocampus; and Right panel—location of imaging slices 1-20. FIG. 3, panel b, shows a T-statistic map from block-design (20 s-on, 40 s-off) subthreshold stimulation of the hippocampus (average over 3 trials). FIG. 3, panel c, shows graphs of fMRI time course (average of 3 trials and single trial) shown for the block-design stimulation paradigm. FIG. 3, panel d, shows a graph of a single trial simultaneously recorded EEG shown for the Beta band 13-30 Hz. FIG. 3, panel e, shows a spectrogram of the EEG recording during fMRI acquisition. Abbreviations: HF—Hippocampal Formation, Sep—Septum.

FIG. 4 shows images and graphs of single subject simultaneous LFP and optogenetic fMRI during seizure-inducing (suprathreshold) stimulation of the hippocampus. FIG. 4, panel a, shows an image of a GLM design matrix for the fMRI analysis. FIG. 4, panel b, shows a T-statistic map showing regions of significant BOLD signal change during a seizure-inducing stimulation (average of 2 trials). FIG. 4, panel c, shows a T-statistic map showing regions of significant BOLD signal change during the first 20 s an epileptiform afterdischarge. Site of optical stimulation is marked by the white triangle. FIG. 4, panel d, shows a segmentation of 4 different ROIs. FIG. 4, panel e, shows a graph of fMRI time course shown for a single trial. FIG. 4, panel f, shows a graph of a single trial simultaneously recorded LFP shown for the Beta band 13-30 Hz. FIG. 4, panel g, shows a spectrogram of the LFP recording during fMRI acquisition. FIG. 4, panel h, shows a graph of fMRI time course for the single trial shown from the ipsilateral hippocampus, septum and contralateral hippocampus. Duration of optical stimulations are marked by blue bars. T-statistic maps were thresholded at a significance level of p<0.01, voxel-wise FDR corrected. Abbreviations: Acb—Accumbens Nucleus, Cpu—Caudate Putamen, RS—Retrosplenial Cortex, Thal—Thalamus, Cg—Cingulate Cortex, HF—Hippocampal Formation, S1—Primary Somatosensory Cortex, Sep—Septum.

FIG. 5 shows images and graphs of group-level analysis of fMRI data. FIG. 5, panel a, shows a first-level (fixed-effects) t-statistic map showing voxels which were significantly activated during subthreshold optogenetic stimulation at 20 Hz. FIG. 5, panel b, shows a first-level (fixed-effects) t-statistic map showing voxels which were significantly activated during seizure-like afterdischarges. Group-level T-statistic maps were thresholded at a significance level of p<0.001, voxel-wise FDR corrected. FIG. 5, panel c, shows a graph of fMRI time courses for subthreshold block-design stimulation from the ipsilateral hippocampus averaged across subjects. FIG. 5, panel d, shows a graph of average LFP band power change from baseline (calculated over each 3 second period) for subthreshold stimulation in the Beta and Theta and Alpha bands. (Error-bars are shown as ±S.E.M.). FIG. 5, panel e, shows a graph of fMRI time courses from the ipsi- and contralateral hippocampi and septum during optogenetically-induced afterdischarges (averaged across subjects). FIG. 5, panel f, shows a graph of average LFP band power change from baseline for the supra threshold stimulation in the Beta and Theta and Alpha bands (Error-bars are shown as ±S.E.M.). FIG. 5, panel g, shows a segmentation of MRI images into different brain regions. Segmented regions are overlaid as colored ROIs on a structural (FSE) MRI image. FIG. 5, panel h, shows a scatter/bar graph showing percentage of significantly activated voxels within a ROI vs. Region of interest for both subthreshold stimulations and seizure-like afterdischarges. Bars indicate the mean value across all 5 subjects and error bars represent ±S.E.M. Significantly activated voxels were considered to be those with a p-value of <0.01, voxel-wise FDR corrected. All panels include n=5 rats. Abbreviations: Acb—Accumbens Nucleus, Amyg—Amygdala, Cpu—Caudate Putamen, M—Motor Cortex, RS—Retrosplenial Cortex, Thal DL—Thalamus Dorsal-Lateral, Thal VM—Thalamus Ventral-Medial, Cg—Cingulate Cortex, Ent—Entorhinal Cortex, HF—Hippocampal Formation, S1—Primary Somatosensory Cortex, Sep—Septum.

FIG. 6 shows images and graphs of ofMRI at different time-averaged light power densities in control (saline injected) rats not expressing ChR2. FIG. 6, panel a, shows T-statistic maps showing regions of significant positive and negative fMRI signal changes at different light power densities (388-2561 mW/mm$^3$). For power levels 388-776 mW/mm$^3$, stimulation paradigms consisted of 20 s trains of 20 Hz, 15 ms pulse duration (30% duty cycle), whereas for the 2561 mW/mm$^3$ level, a 99% duty cycle was used at 10 Hz. FIG. 6, panel b, shows a bar graph displaying mean percentage of ROI exhibiting significant negative fMRI signal change at different power levels (n=3 for 388-776 mW/mm$^3$ and n=2 for 2561 mW/mm$^3$). Quantification was performed using a circular ROI placed below the optrode and consisted of 7 voxels in diameter across 2 consecutive slices (right panel). Site of optical stimulation is marked by an inverted triangle. T-statistic maps were thresholded at a significance level of p<0.01, voxel-wise FDR corrected. These data indicated that the time-averaged light-intensity range used for ofMRI experiments (56-167 mW/mm$^2$) was far below the range that generated artifactual responses.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An implantable device comprising an optrode comprising:
    a carbon fiber electrode having a first end and a second end, wherein the carbon fiber electrode has a diameter of from 10 μm to 180 μm;
    a metal wire or metal connector attached to the carbon fiber electrode at the first end;
    a ceramic stick ferrule having a third end and a fourth end, wherein the ceramic stick ferrule has a face at the third end, wherein the face has a first diameter less than a second diameter of the fourth end; and
    an optical fiber having a fifth end and a sixth end, wherein a portion of the optical fiber proximate the fifth end is located within the ceramic stick ferrule, wherein the optical fiber is inserted into a concave face of the ceramic stick ferrule such that the fifth end is level with the face of the third end of the ceramic stick ferrule, wherein the third end of the ceramic stick ferrule is configured to be coupled to a light source and a remaining portion of the optical fiber including the sixth end extends from the fourth end of the ceramic stick ferrule, wherein the optical fiber is secured within the ceramic stick ferrule by a first epoxy,
    wherein a first portion of the carbon fiber electrode proximate the second end is coupled to a portion of optical fiber proximate the sixth end by a second epoxy such that the portion of the carbon fiber electrode and the portion of the optical fiber are aligned parallel to one another and the second end of the carbon fiber electrode and the sixth end of the optical fiber are aligned such that neither the second end nor the sixth end extends further than the other and the second end and the sixth end are configured to be implanted in a subject, wherein a second portion of the carbon fiber electrode between the first portion and the first end is coupled to a portion of the ceramic stick ferrule proximate the fourth end by a third epoxy.

2. The device of claim 1, wherein the carbon fiber electrode has a diameter of from 100 μm to 150 μm.

3. The device of claim 1, wherein the carbon fiber electrode comprises a bundle of carbon fibers.

4. The device of claim 3, wherein the bundle of carbon fibers comprises 1000 or less carbon fibers.

5. The device of claim 1, wherein the carbon fiber electrode comprises an insulation coating.

6. The device of claim 5, wherein the insulation coating comprises a thermoplastic polyvinylidene fluoride (PVDF), wherein the PVDF is diluted with methyl isobutyl ketone.

7. The device of claim 1, wherein the carbon fiber electrode is attached to the metal wire or the metal connector with a conductive adhesive, wherein the conductive adhesive is a conductive epoxy adhesive.

8. The device of claim 1, wherein the carbon fiber electrode has an impedance magnitude of 200 kΩ or less at 100 Hz in 0.9% (w/v) sodium chloride in water.

9. The device of claim 1, wherein the optrode is adapted for use in magnetic resonance imaging.

10. The device of claim 1, further comprising the light source coupled to the optical fiber.

11. The device of claim 10, wherein the light source comprises a laser.

12. A method for monitoring activity in an excitable organ or tissue, the method comprising:

a) surgically implanting the device of claim 1 into an excitable organ or tissue of a subject; and
b) monitoring the activity of the organ or tissue by:
  i) conducting functional magnetic resonance imaging on the organ or tissue, wherein the organ or tissue comprises cells that express one or more light-responsive polypeptides; and/or
  ii) recording a detectable parameter of the organ or tissue using the device.

13. The method of claim 12, wherein the detectable parameter comprises one or more of local field potentials, single-unit activity, and multi-unit activity in the organ or tissue.

14. The method of claim 12, wherein the monitoring comprises chronically monitoring the activity of the organ or tissue.

15. The method of claim 14, wherein the recording is performed 10 days or more after implanting the device.

16. The method of claim 12, wherein the one or more light-responsive polypeptides comprises a hyperpolarizing light-responsive polypeptide.

17. The method of claim 12, wherein the one or more light-responsive polypeptides comprises a depolarizing light-responsive polypeptide.

18. The method of claim 12, wherein the device comprises the light source coupled to the optical fiber, and the method comprises delivering light to the organ or tissue using the light source.

19. The device of claim 1, wherein the metal wire or metal connector is attached to the carbon fiber electrode with a conductive adhesive.

20. The device of claim 19, wherein the conductive adhesive comprises graphite.

* * * * *